US 9,496,508 B2

United States Patent
Shiomi et al.

(10) Patent No.: US 9,496,508 B2
(45) Date of Patent: Nov. 15, 2016

(54) MATERIAL FOR ORGANIC ELECTROLUMINESCENT ELEMENT AND ORGANIC ELECTROLUMINESCENT ELEMENT USING SAME

(71) Applicant: Idemitsu Kosan Co., Ltd., Chiyoda-ku, Tokyo (JP)

(72) Inventors: Takushi Shiomi, Sodegaura (JP); Ryohei Hashimoto, Sodegaura (JP); Hideaki Nagashima, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 414 days.

(21) Appl. No.: 14/363,761

(22) PCT Filed: Dec. 5, 2012

(86) PCT No.: PCT/JP2012/007789
§ 371 (c)(1),
(2) Date: Jun. 6, 2014

(87) PCT Pub. No.: WO2013/084484
PCT Pub. Date: Jun. 13, 2013

(65) Prior Publication Data
US 2014/0353650 A1  Dec. 4, 2014

(30) Foreign Application Priority Data

Dec. 7, 2011 (JP) ................................. 2011-268228

(51) Int. Cl.
*H01L 51/50* (2006.01)
*H01L 51/00* (2006.01)
(Continued)

(52) U.S. Cl.
CPC ......... *H01L 51/0072* (2013.01); *C07D 235/18* (2013.01); *C07D 401/04* (2013.01); *C07D 401/14* (2013.01); *C07D 403/14* (2013.01); *C07D 405/14* (2013.01); *C07D 409/14* (2013.01); *C07D 413/14* (2013.01);

*C07D 471/04* (2013.01); *C07D 519/00* (2013.01); *C09K 11/06* (2013.01);
(Continued)

(58) Field of Classification Search
None
See application file for complete search history.

(56) References Cited

FOREIGN PATENT DOCUMENTS

EP    2 497 811 A2    9/2012
JP    2006-131783     5/2006
(Continued)

OTHER PUBLICATIONS

International Search Report issue in International Application No. PCT/JP2012/007789 dated Feb. 19, 2013.
(Continued)

*Primary Examiner* — Gregory Clark
(74) *Attorney, Agent, or Firm* — Foley & Lardner LLP

(57) ABSTRACT

A compound represented by the following formula (1).

(1)

[Chemical structure diagram showing a compound with substituents $A_1$, $A_2$, $X_1$ through $X_{15}$, containing cyclopentadiene and pyrrole rings connected via a methine linker]

16 Claims, 1 Drawing Sheet

1: Organic EL device

| 60: Cathode |
| 50: Electron-transporting region |
| 40: Phosphorescent emitting layer |
| 30: Hole-transporting region |
| 20: Anode |
| 10: Substrate |

(51) Int. Cl.
*C07D 401/14* (2006.01)
*C09K 11/06* (2006.01)
*H05B 33/20* (2006.01)
*C07D 405/14* (2006.01)
*C07D 413/14* (2006.01)
*C07D 401/04* (2006.01)
*C07D 235/18* (2006.01)
*C07D 403/14* (2006.01)
*C07D 409/14* (2006.01)
*C07D 471/04* (2006.01)
*C07D 519/00* (2006.01)

(52) U.S. Cl.
CPC ...... *H05B 33/20* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1033* (2013.01); *C09K 2211/1044* (2013.01); *C09K 2211/1059* (2013.01); *C09K 2211/1088* (2013.01); *C09K 2211/1092* (2013.01); *H01L 51/5016* (2013.01); *H01L 51/5044* (2013.01); *H01L 51/5072* (2013.01); *H01L 51/5092* (2013.01); *H01L 51/5096* (2013.01); *H01L 2251/5376* (2013.01)

(56) References Cited

FOREIGN PATENT DOCUMENTS

| JP | 2010-114180 | * | 5/2010 | ............ H01L 51/50 |
| JP | 2011-054931 A | | 3/2011 | |
| KR | 2012-072787 | * | 7/2012 | ............ H01L 51/50 |
| KR | 10-2012-0092908 A | | 8/2012 | |
| WO | WO-2011/055934 A2 | | 5/2011 | |

OTHER PUBLICATIONS

Seyhan, S., et al, Theoretical Investigation of Triscarbazole Derivatives as Host Materials for Blue Electrophosphorescence: Effects of Topology, Chemistry of Materials, Nov. 7, 2011, vol. 23, Issue 23, pp. 5223-5230.

Written Opinion of the International Searching Authority issued in International Application No. PCT/JP2012/007789 dated Jun. 19, 2014.

Xin, G., et al, Bipolar Host Molecules for Efficient Blue Electrophosphorescence: A Quantum Chemical Design, Journal of Physical Chemistry A, 2010, vol. 114, Issue 2, pp. 965-972.

Min-Gi Shin et al., Organic Electronics 12 (2011), p. 785-793.

* cited by examiner

MATERIAL FOR ORGANIC ELECTROLUMINESCENT ELEMENT AND ORGANIC ELECTROLUMINESCENT ELEMENT USING SAME

CROSS REFERENCE TO RELATED APPLICATIONS

This application is the National Phase of PCT/JP2012/007789, filed Dec. 5, 2012, which claims priority to Japanese Application No. 2011-268228, filed Dec. 7, 2011.

TECHNICAL FIELD

The invention relates to a novel compound suited for a material for an organic electroluminescence device, and an organic electroluminescence device using the same.

BACKGROUND ART

Organic electroluminescence (EL) devices are divided into two types, i.e. a fluorescent type and a phosphorescent type. For each type, an optical device design has been studied according to the emission mechanism. For the phosphorescent organic EL device, it is known that due to its emission properties, a high-performance device cannot be obtained by simple application of the fluorescent device technique. The reason therefor is generally considered as follows.

The phosphorescent emission utilizes triplet excitons and thus a compound used in an emitting layer has to have a large energy gap, since the energy gap value (hereinafter also referred to as singlet energy) of a compound is normally larger than the triplet energy value (referred to as the difference in energy between the lowest excited triplet state and the ground state in the invention) of the compound.

Therefore, in order to confine the triplet energy of a phosphorescent dopant material in an emitting layer efficiently, it is required that a host material having a larger triplet energy than that of a phosphorescent dopant material be used in the emitting layer. In addition, it is required that an electron-transporting layer and a hole-transporting layer be provided adjacent to the emitting layer, and compounds having a triplet energy larger than that of the phosphorescent dopant material be used in the electron-transporting layer and the hole-transporting layer.

As seen above, designing an organic EL device based on the traditional design concept leads to the use in the phosphorescent organic EL device a compound having a larger energy gap than that of a compound used in the fluorescent organic EL device, thereby to increase the driving voltage of the whole organic EL device.

In addition, a hydrocarbon-based compound having a high oxidation resistance and a high reduction resistance, which is useful for a fluorescent device, has a broad pi-electron cloud, and hence a small energy gap. Thus, for the phosphorescent organic EL device, such a hydrocarbon-based compound is unlikely to be selected, but an organic compound containing a hetero atom such as oxygen or nitrogen is rather selected. Consequently, the phosphorescent organic EL device has a problem that it has a shorter life as compared with the fluorescent organic EL device.

Further, the device performance is greatly affected by the fact that the relaxation rate of triplet excitons of a phosphorescent dopant material is very slower than that of singlet excitons thereof. That is, the emission from singlet excitons is expected to be efficient, since the rate of the relaxation leading to the emission is so rapid that excitons are unlikely to diffuse to the neighboring layers of an emitting layer (hole-transporting layer or electron-transporting layer, for example). On the other hand, since emission from triplet excitons is spin-forbidden and has a slow relaxation rate, the triplet excitons are likely to diffuse to the neighboring layers, so that the triplet excitons are thermally energy-deactivated unless the phosphorescent dopant material is a specific phosphorescent compound. In short, in the phosphorescent organic EL device, control of electrons and holes in the recombination region is more important as compared with the fluorescent organic EL device.

For the above reasons, enhancement of the performance of a phosphorescent organic EL device requires material selection and device design different from those of a fluorescent organic EL device.

In addition, when a device has a structure in which the pi-conjugated bond is cut in order to enhance the triplet energy of a compound, the transporting property of carriers tends to lower. That is, the pi-conjugated bond is required to be extended for higher transporting property of carriers. However, doing so causes a problem that the triplet energy is lowered.

Under such conditions, Non-Patent Document 1 discloses the use of an N-fluorenyl carazole compound as a material for an organic EL device, for example.

RELATED ART DOCUMENTS

Non-Patent Documents

Non-Patent Document 1: Organic Electronics 12 (2011), P. 785-793

SUMMARY OF THE INVENTION

The invention is aimed at providing a material which can be used as a material for a blue phosphorescent organic EL device and has high triplet energy.

According to the invention, the following compounds, materials for an organic EL device and organic EL devices are provided.

1. A compound represented by the following formula (1):

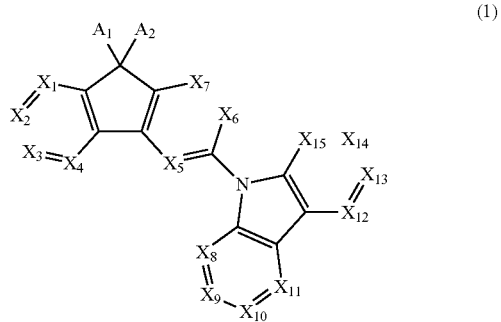

wherein $X_1$ to $X_7$ are independently a nitrogen atom, or a carbon atom that $R_1$ is bonded to, provided that at least one of $X_1$ to $X_7$ is a nitrogen atom;

R₁ represents a hydrogen atom, a substituted or unsubstituted alkyl group including 1 to 20 carbon atoms, a substituted or unsubstituted cycloalkyl group including 3 to 18 carbon atoms that form a ring (hereinafter referred to as the "ring carbon atoms"), a substituted or unsubstituted alkoxy group including 1 to 20 carbon atoms, a substituted or unsubstituted cycloalkoxy group including 3 to 18 ring carbon atoms, a substituted or unsubstituted silyl group, or a fluoro group, and when two or more R₁s are present in the formula (1), R₁s may be the same or different from each other;

X₈ to X₁₅ are independently a nitrogen atom, or a carbon atom that R₂ is bonded to;

R₂ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 atoms that form a ring (hereinafter referred to as the "ring atoms"), a substituted or unsubstituted amino group, a substituted or unsubstituted silyl group, a fluoro group, or a cyano group, and when two or more R₂s are present in the formula (1), R₂s may be the same or different from each other; and A₁ and A₂ are independently a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

2. The compound according to 1, which is a compound represented by the following formula (2):

R₃ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, and when two or more R₃s are present in the formula (2), R₃s may be the same or different from each other;

Y represents an oxygen atom (O), a sulfur atom (S) or NR₄;

R₄ represents a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group;

W represents a single bond, O, S, P(R₅), P(=O)(R₆), N(R₇), Si(R₈)(R₉) or C(R₁₀)(R₁₁); and R₅ to R₁₁ independently represent a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, provided that one carbon atom selected from X₁₂ to X₁₅ is bonded through a single (2)

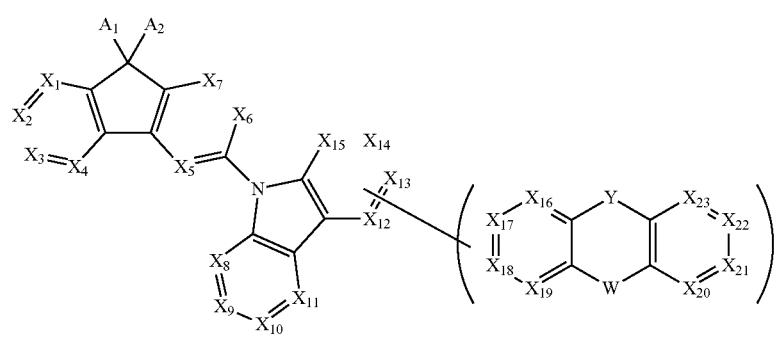

wherein X₁ to X₁₅, A₁ and A₂ independently represent the same as in the formula (1);

X₁₈ to X₂₃ are independently a nitrogen atom, or a carbon atom that R₃ is bonded to;

bond to one carbon atom selected from X₁₆ to X₁₉ or a nitrogen atom when Y is NR₄.

3. The compound according to 2, which is a compound represented by the following formula (3):

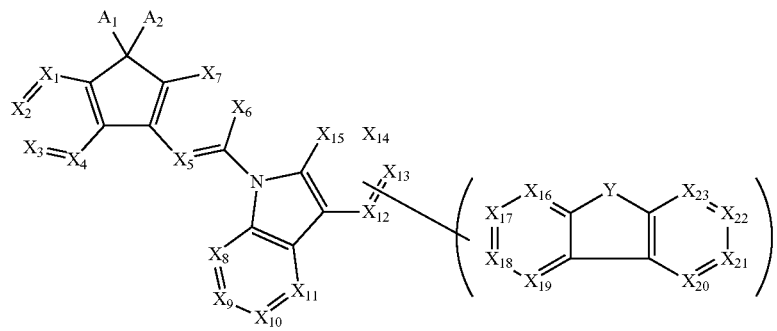

(3)

wherein $X_1$ to $X_{23}$, $A_1$, $A_2$ and Y independently represent the same as in the formula (2).

4. The compound according to 2 or 3, which is a compound represented by the following formula (4):

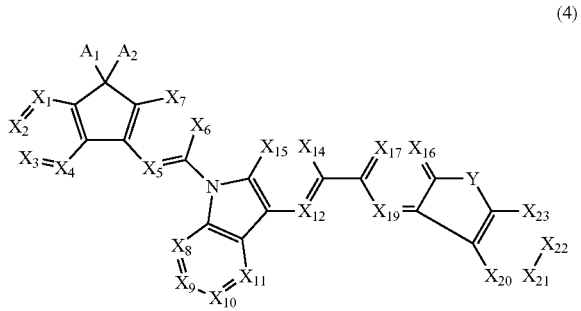

(4)

wherein $X_1$ to $X_{12}$, $X_{14}$ to $X_{17}$, $X_{19}$ to $X_{23}$, $A_1$, $A_2$ and Y independently represent the same as in the formula (2).

5. The compound according to any one of 2 to 4, which is a compound represented by the following formula (5):

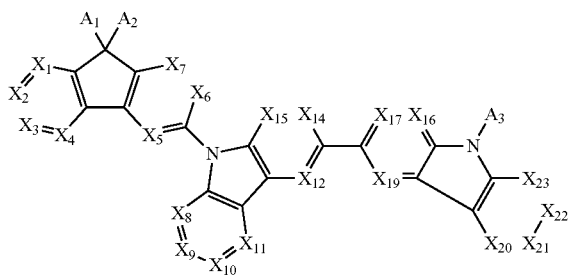

(5)

wherein $X_1$ to $X_{12}$, $X_{14}$ to $X_{17}$, $X_{19}$ to $X_{23}$, $A_1$ and $A_2$ independently represent the same as in the formula (2); and $A_3$ represents a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

6. The compound according to 2 or 3, which is a compound represented by the following formula (6):

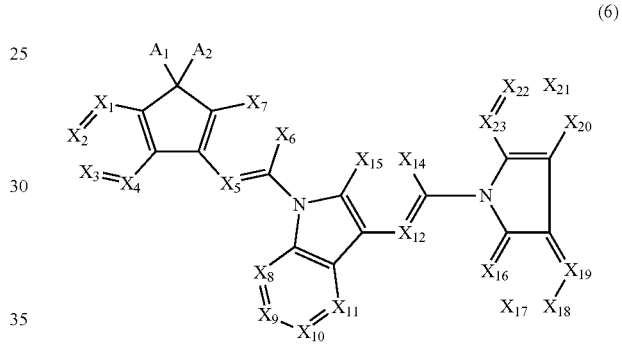

(6)

wherein $X_1$ to $X_{12}$, $X_{14}$ to $X_{23}$, $A_1$ and $A_2$ independently represent the same as in the formula (2).

7. The compound according to any one of 1 to 6, wherein at least one of $X_1$ to $X_4$ and $X_7$ is N.

8. A material for an organic electroluminescence device comprising the compound according to any one of 1 to 7.

9. An organic electroluminescence device comprising one or more organic thin film layers including an emitting layer between a cathode and an anode, wherein at least one layer of the organic thin film layers comprises the material for an organic electroluminescence device according to 8.

10. The organic electroluminescence device according to 9, wherein the organic emitting layer comprises the material for an organic electroluminescence device.

11. The organic electroluminescence device according to 9 or 10, wherein the organic emitting layer comprises a phosphorescent material, the phosphorescent material being an ortho-metalated complex of a metal atom selected from iridium (Ir), osmium (Os) and platinum (Pt).

12. The organic electroluminescence device according to any one of 9 to 11, which comprises an electron-transporting region between the cathode and the emitting layer, the electron-transporting region comprising the material for an organic electroluminescence device.

13. The electroluminescence device according to any one of 9 to 12, which comprises an electron-injecting layer between the organic emitting layer and the cathode, the electron-injecting layer comprising a nitrogen-containing ring derivative.

According to the invention, a compound having high triplet energy and high carrier-transporting property can be provided. The compound is suited for a material for an organic EL device.

MODE FOR CARRYING OUT THE INVENTION

Figure 1:
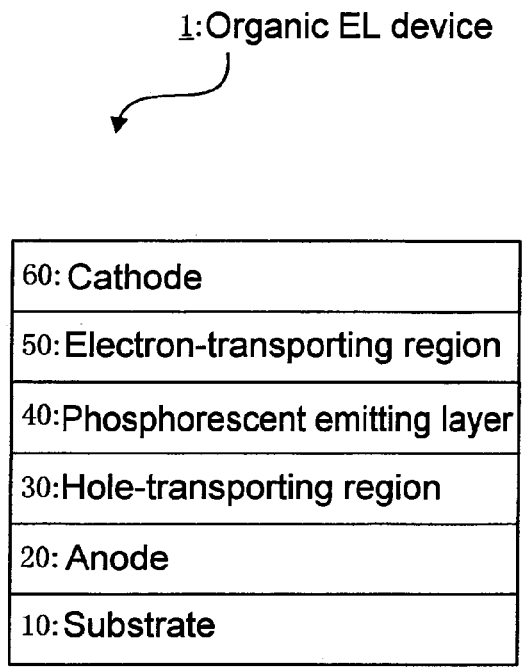
FIG. 1 is a schematic view showing the layer construction according to one embodiment of the organic EL device of the invention.

The compound of the invention is represented by the following formula (1).

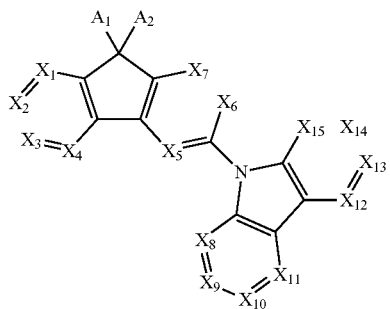

The compound represented by the formula (1) has a structure in which an aza-fluorenyl group and a group having a carbazole analogous skeleton are bonded at a specific position. Although an aza-fluorenyl group has a high electron-transporting property, its triplet energy (T1) is low. As a result, when the group is used as a host in an emitting layer of a blue phosphorescent device, the efficiency of the resulting device is insufficient.

However, when the site corresponding to the 3th position of the fluorene ring in the aza-fluorenyl group and the 9$^{th}$ position of the carbazole analogous group are bonded to each other as shown in the formula (1), the resulting compound can have a high triplet energy while it maintains a high carrier-transporting property.

In the formula (1), $X_1$ to $X_7$ are independently a nitrogen atom, or a carbon atom that $R_1$ is bonded to, provided that at least one of $X_1$ to $X_7$ is a nitrogen atom.

$R_1$ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted silyl group, or a fluoro group, and when two or more $R_1$s are present in the formula (1), $R_1$s may be the same or different from each other.

In the formula (1), $R_1$ bonded to the aza-fluorenyl group is neither an aryl group nor a heteroaryl group. If the aza-fluorenyl group has the substituents of these aromatic rings, the compound represented by the formula (1) cannot keep the triplet energy high due to the spread conjugated system of the compound.

$X_8$ to $X_{15}$ are independently a nitrogen atom, or a carbon atom that $R_2$ is bonded to.

$R_2$ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, and when two or more $R_2$s are present in the formula (1), $R_2$s may be the same or different from each other.

$A_1$ and $A_2$ are independently a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

Of the compounds of the formula (1), a compound represented by the following formula (2) is preferable.

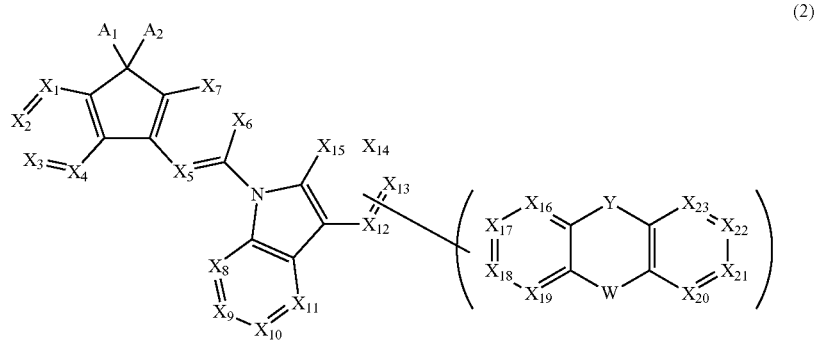

In the formula (2), $X_1$ to $X_{15}$, $A_1$ and $A_2$ independently represent the same as in the formula (1). The compound of the formula (2) is a compound in which one of $X_{12}$ to $X_{15}$ in the formula (1) is bonded through a single bond to the group in parenthesis.

$X_{16}$ to $X_{23}$ are independently a nitrogen atom, or a carbon atom that $R_3$ is bonded to.

$R_3$ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, and when two or more $R_3$s are present in the formula (2), $R_3$s may be the same or different from each other.

Y represents an oxygen atom (O), a sulfur atom (S) or $N(R_4)$.

$R_4$ represents a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

W represents a single bond, O, S, $P(R_5)$, $P(=O)(R_6)$, $N(R_7)$, $Si(R_8)(R_9)$ or $C(R_{10})(R_{11})$.

$R_5$ to $R_{11}$ independently represent a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

In the formula (2), one carbon atom selected from $X_{12}$ to $X_{15}$ is bonded through a single bond to one carbon atom selected from $X_{16}$ to $X_{19}$ or a nitrogen atom when Y is $NR_4$. In the case, the nitrogen atom is not bonded to $R_4$ but to a carbon atom selected from $X_{12}$ to $X_{15}$.

Of the compounds of the formula (2), a compound represented by the following formula (3) in which W is a single bond is preferable.

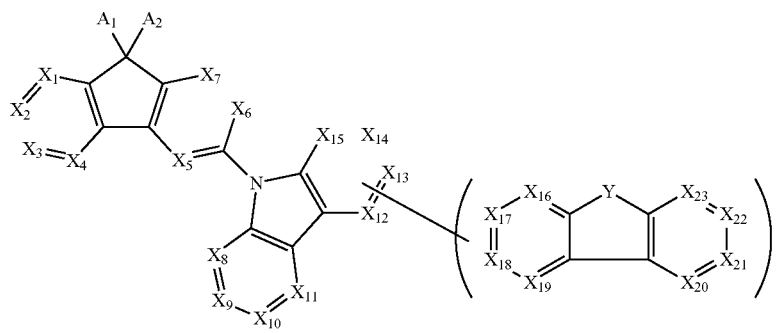

(3)

wherein $X_1$ to $X_{23}$, $A_1$, $A_2$ and Y independently represent the same as in the formula (2).

Further, a compound represented by the following formula (4) is preferable.

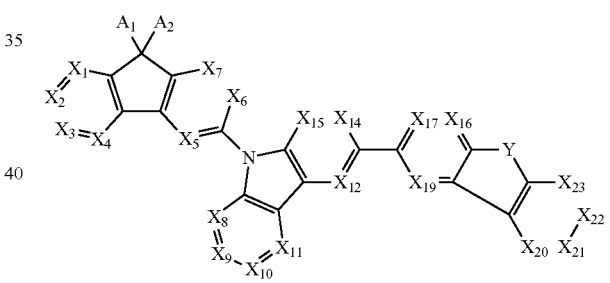

(4)

wherein $X_1$ to $X_{12}$, $X_{14}$ to $X_{17}$, $X_{19}$ to $X_{23}$, $A_1$, $A_2$ and Y independently represent the same as in the formula (2).

Particularly, a compound represented by the following formula (5) is preferable.

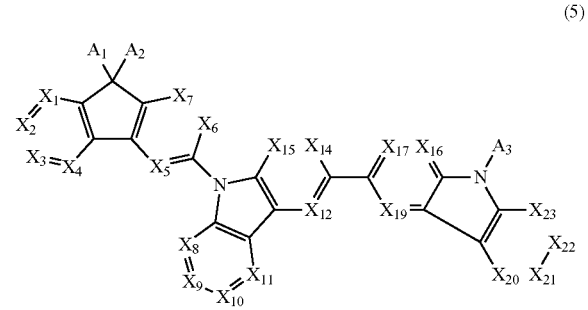

(5)

wherein $X_1$ to $X_{12}$, $X_{14}$ to $X_{17}$, $X_{19}$ to $X_{23}$, $A_1$ and $A_2$ independently represent the same as in the formula (2). $A_3$ represents the same as the above-mentioned $R_4$.

In the formula (5), $A_3$ is preferably a substituted or unsubstituted heteroaryl group including 5 to 18 ring atoms. In particular, a group represented by the following formula is preferable.

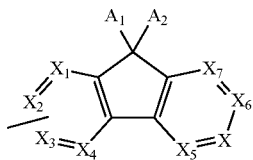

wherein $X_1$ to $X_7$, $A_1$ and $A_2$ independently represent the same as in the formula (1). X represents the same as $X_1$ to $X_7$. At least one of $X_1$ to $X_7$ and X is a nitrogen atom, provided that at least one of $X_1$ to $X_7$ and X is bonded through a single bond to an N atom in the formula (5).

Also, a compound represented by the following formula (6) is preferable.

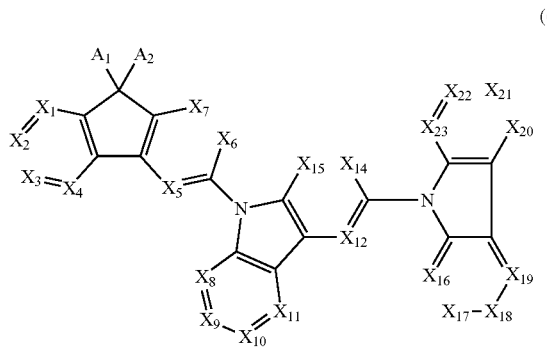

(6)

wherein $X_1$ to $X_{12}$, $X_{14}$ to $X_{23}$, $A_1$ and $A_2$ independently represent the same as in the formula (2)

In the formulas (1) to (6), at least one of $X_1$ to $X_4$ and $X_7$ is preferalbly N.

Examples of each group in the formulas (1) to (6) will be explained bellow.

In the specification, the aryl group includes a monocyclic aromatic hydrocarbon ring group and a fused aromatic hydrocarbon ring group obtained by fusing plural hydrocarbon rings. The heteroaryl group includes a monocyclic hetero aromatic ring group, and a hetero fused aromatic ring group obtained by fusing plural hetero aromatic rings, and a hetero fused aromatic ring group obtained by fusing an aromatic hydrocarbon ring and a hetero aromatic ring.

The term "unsubstituted" in "substituted or unsubstituted" means the state substituted by a hydrogen atom. The hydrogen atom in the material of the invention includes protium, deuterium and tritium.

Specific examples of the alkyl group including 1 to 20 carbon atoms include a methyl group, an ethyl group, a propyl group, an isopropyl group, an n-butyl group, an s-butyl group, an isobutyl group, a tert-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methypentyl group, a 1-pentylhexyl group, a 1-butylpentyl group, a 1-heptyloctyl group and a 3-methylpentyl group. The above-mentioned alkyl group preferably includes 1 to 6 carbon atoms.

Specific examples of the cycloalkyl group including 3 to 18 ring carbon atoms include a cyclopropyl group, a cyclobutyl group, a cyclopentyl group, a cyclohexyl group, a cycloheptyl group, a norbornyl group and an adamantyl group. The above-mentioned cycloalkyl group preferably includes 5 or 6 ring carbon atoms.

Meanwhile, the "carbon atoms that form a ring" means carbon atoms constituting a saturated ring, an unsaturated ring or an aromatic ring.

As the alkoxy group including 1 to 20 carbon atoms, a methoxy group, an ethoxy group, a propoxy group, a penthyloxy group, a hexyloxy group or the like can be given. The alkoxy group including 3 or more carbon atoms may be a linear or branched one. The above-mentioned alkoxy group preferably includes 1 to 6 carbon atoms.

As the cycloalkoxy group including 3 to 18 ring carbon atoms, a cyclopenthoxy group, a cyclohexyloxy group or the like can be given. The above-mentioned cycloalkoxy group preferably includes 5 or 6 ring carbon atoms.

Specific examples of the aryl group including 6 to 18 ring carbon atoms include a phenyl group, a tolyl group, a xylyl group, a mesityl group, an o-biphenyl group, an m-biphenyl group, a p-biphenyl group, an o-terphenyl group, an m-terphenyl group, a p-terphenyl group, a naphthyl group, a phenanthryl group and a triphenylenyl group. Of these, a phenyl group is preferable.

As the aryloxy group including 6 to 18 ring carbon atoms, a phenoxy group, a biphenoxy group or the like can be given. A phenoxy group is preferable.

Specific examples of the heteroaryl group including 5 to 18 ring atoms include a pyrrolyl group, a pyrazinyl group, a pyridinyl group, a pyrimidinyl group, a pyridazinyl group, a triazinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, an azacarbazolyl group, a phenanthridinyl group, an acridinyl group, a phenanthrolinyl group, a thienyl group, a pyrrolidinyl group, a dioxanyl group, a piperidynyl group, a morpholinyl group, a piperazinyl group, a carbazolyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzimidazolyl group, a pyranyl group and a benzo[c]dibenzofuranyl group. The above-mentioned heteroaryl group preferably includes 6 to 14 ring atoms.

Meanwhile, the "atoms that form a ring" means atoms constituting a saturated ring, an unsaturated ring or an aromatic ring.

As the substituted or unsubstituted amino group, an amino group, an alkylamino group and dialkylamino group including 1 to 10 (preferably 1 to 6) carbon atoms, an arylamono group and diarylamino group including 6 to 30 (preferably 6 to 20, more preferably 6 to 10) carbon atoms and the like can be given.

Preferable is a diphenylamino group.

As the substituted or unsubstituted silyl group, a silyl group, an alkylsilyl group including 1 to 10 (preferably 1 to 6) carbon atoms, an arylsilyl group including 6 to 30 (preferably 6 to 20, more preferably 6 to 10) carbon atoms and the like can be given.

Specific examples of the alkylsilyl group include a trimethysilyl group, a triethylsilyl group, a t-butyldimethylsilyl group, a vinyldimethylsilyl group and a propyldimethylsilyl group.

Specific examples of the arylsilyl group include a triphenylsilyl group, a phenyldimethylsilyl group, a t-butyldiphenylsilyl group, a tritolylsilyl group, a trixylylsilyl group and a trinaphtylsilyl group.

As the substituent of "substituted or unsubstituted" for each of the above-mentioned groups, in addition to the above-mentioned alkyl group, substituted or unsbstituted amino group, substituted or usubstituted silyl group, aromatic hydrocarbon ring group, cycloalkyl group, hetero aromatic ring group and alkoxy group, a halogen atom (fluorine, chlorine, bromine, iodine and the like can be given, fluorine is preferable), a fluoroalkyl group, a hydroxyl group, a nitro group, a cyano group, a carboxy group, an aryloxy group and the like can be given.

Specific examples of the compound represented by the formula (1) are shown below.

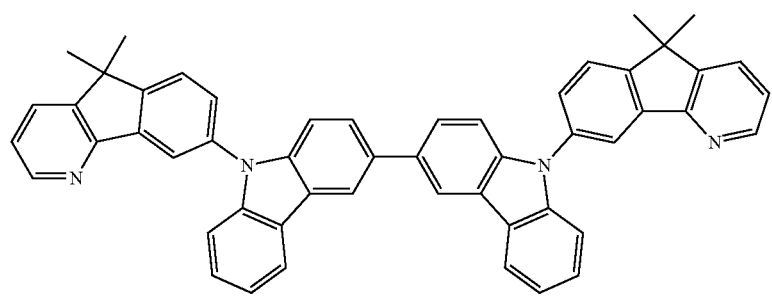

(1)

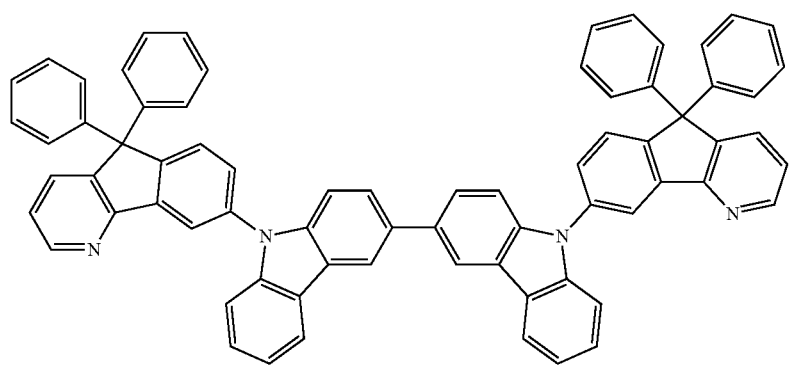

(2)

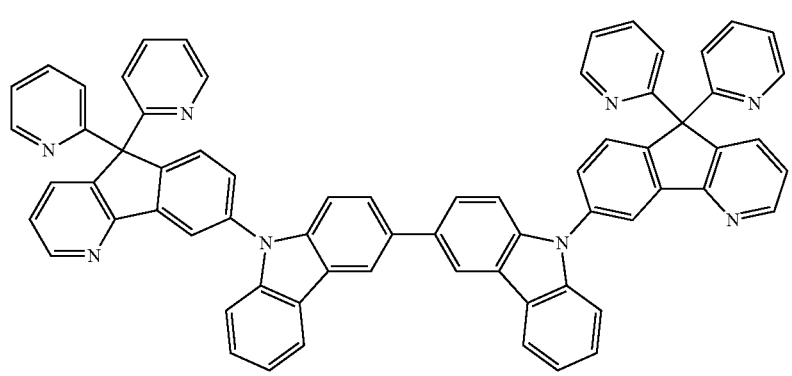

(3)

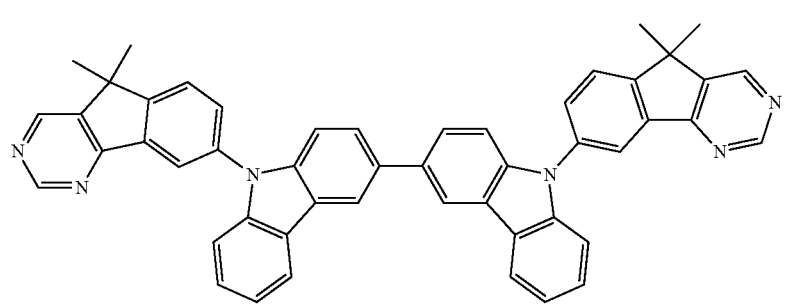

(4)

-continued
(5)
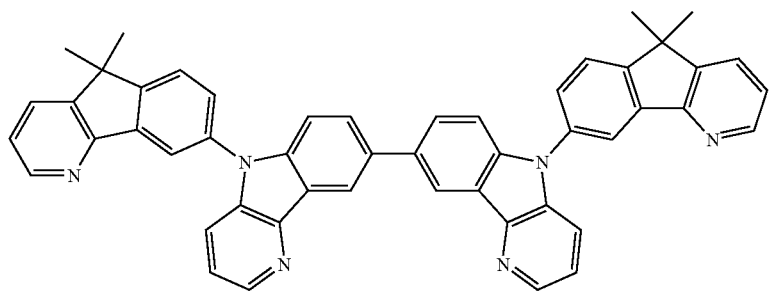
(6)
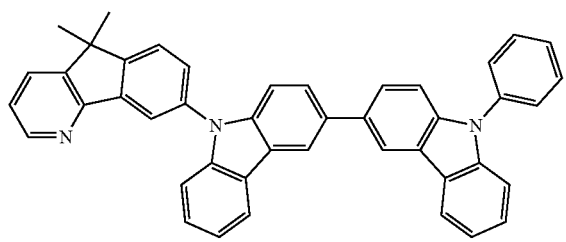
(7)
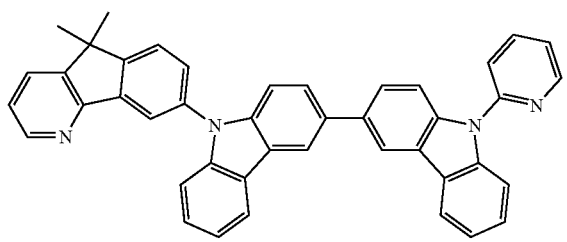
(8)
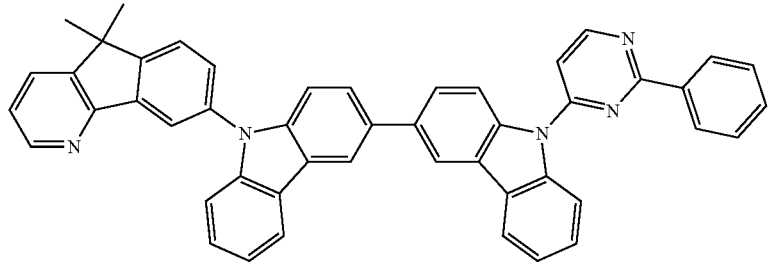
(9)
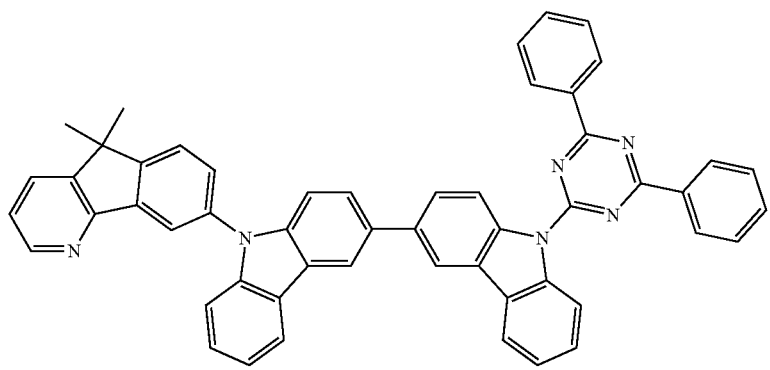
(10)
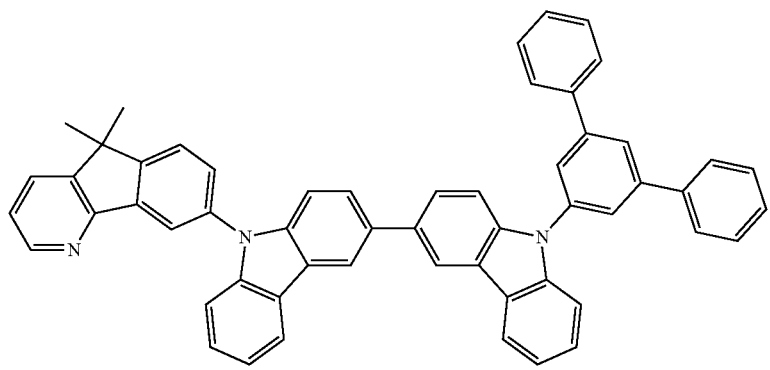

-continued
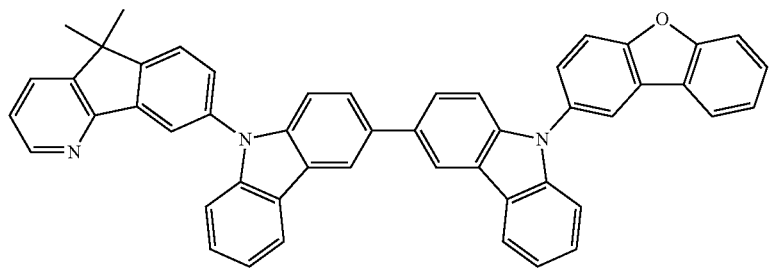
(11)
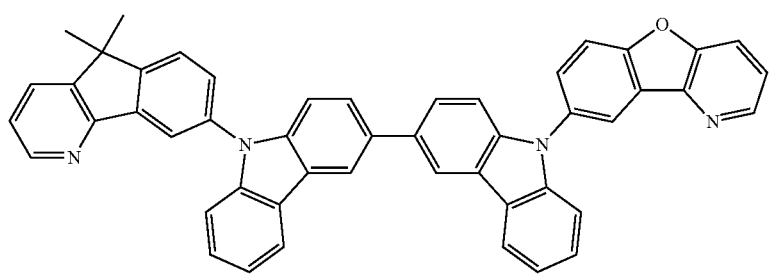
(12)
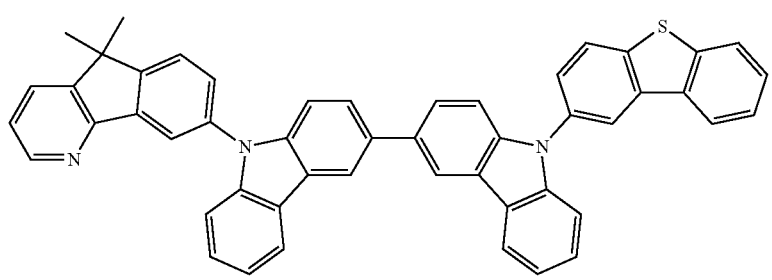
(13)
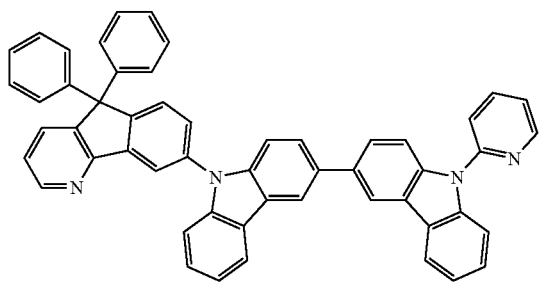
(14)
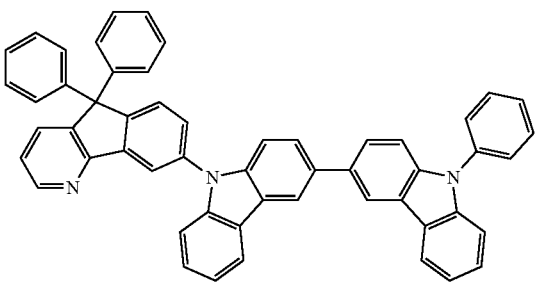
(15)
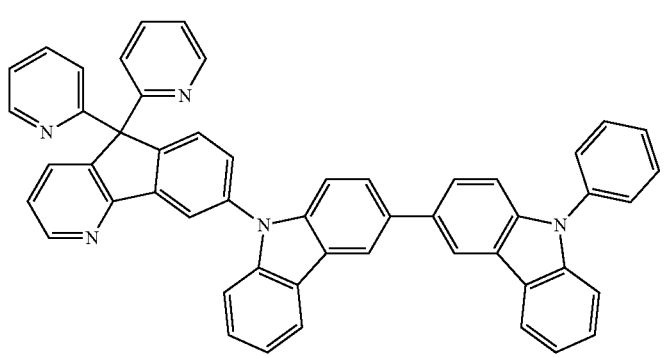
(16)

-continued
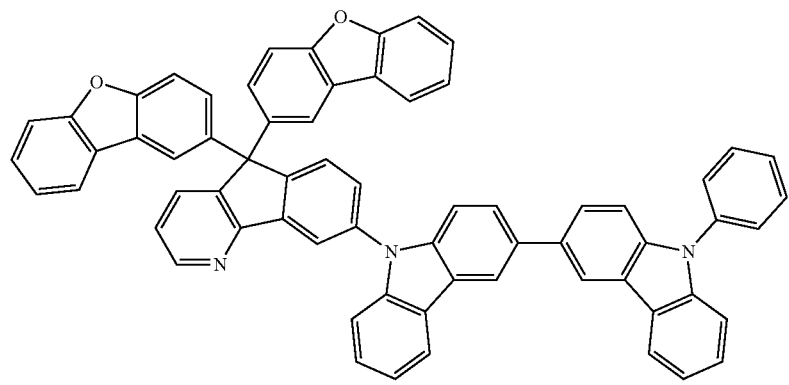
(17)
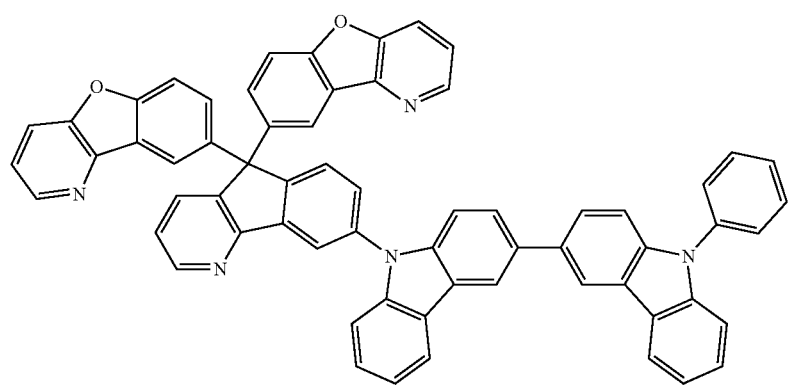
(18)
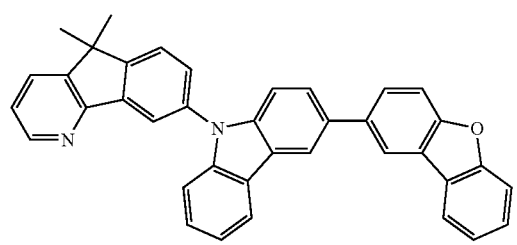
(19)
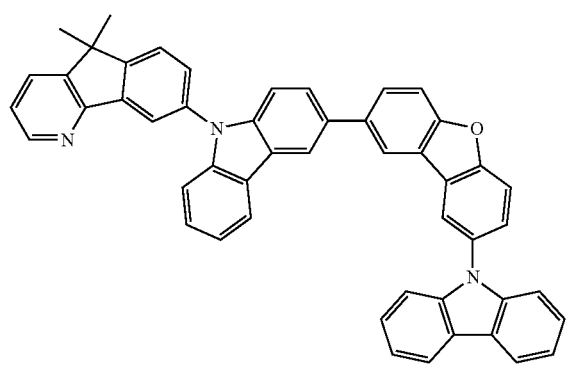
(20)
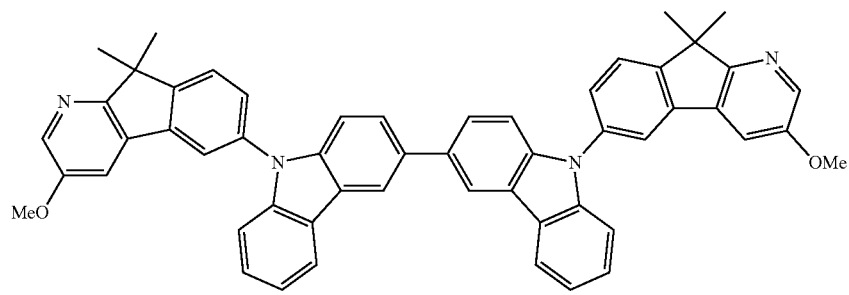
(21)

-continued
(22)
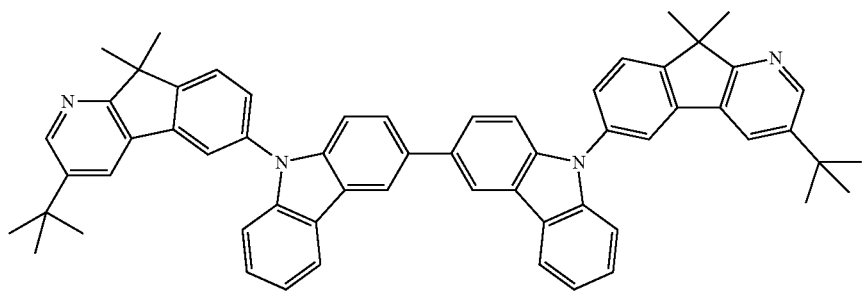
(23)
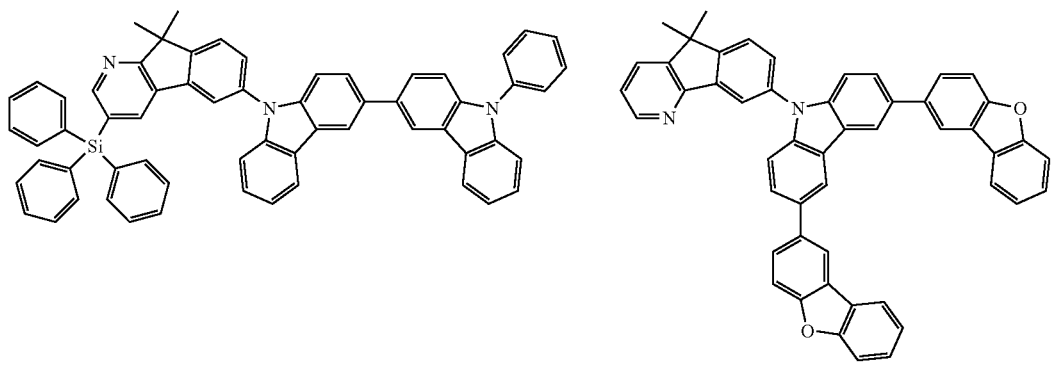
(24)
(25)
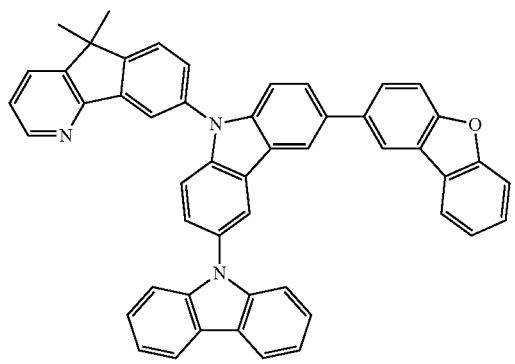
(26)
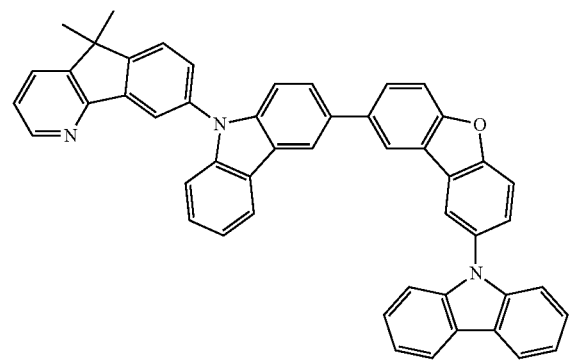
(27)
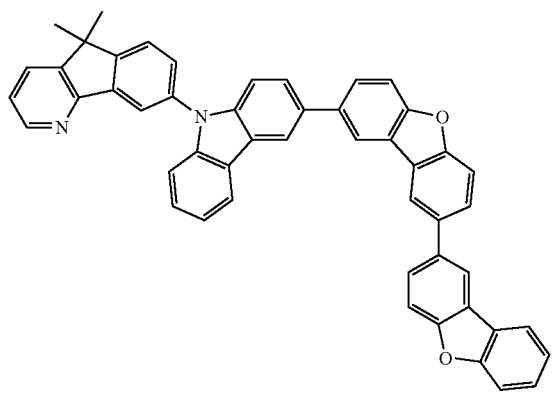
(28)
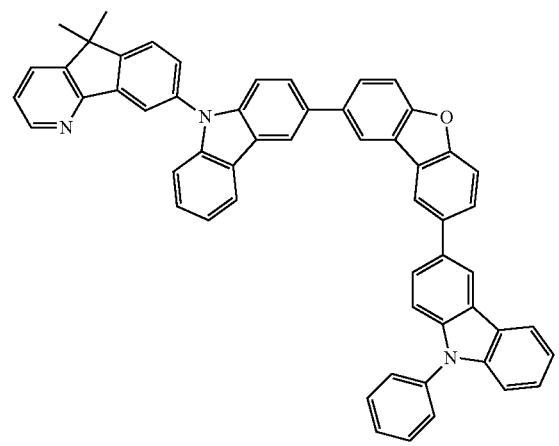

-continued
(29)
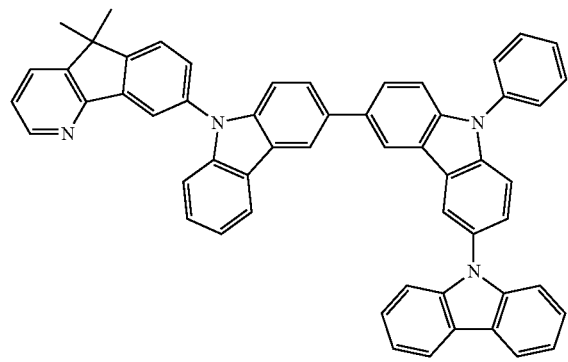
(30)
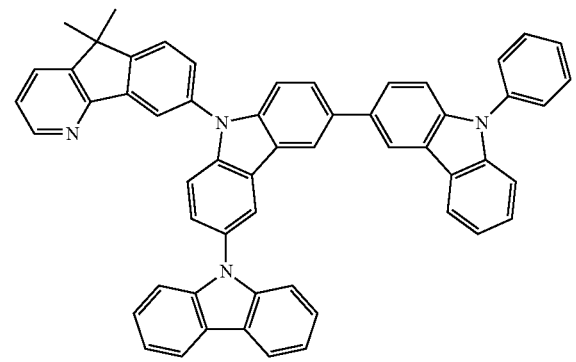
(31)
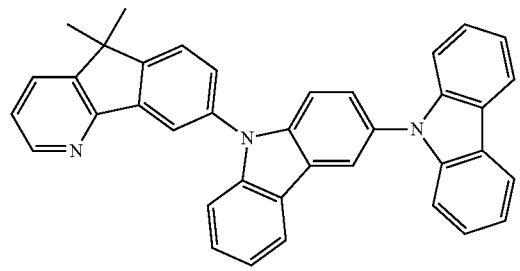
(32)
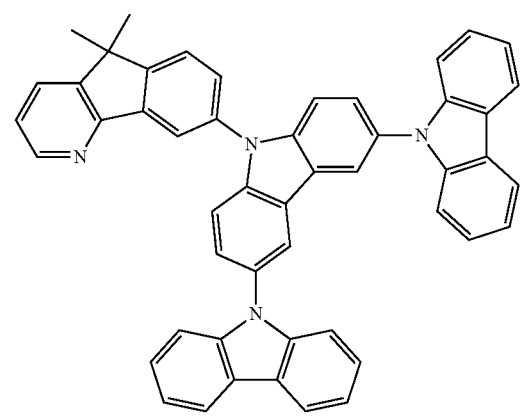
(33)
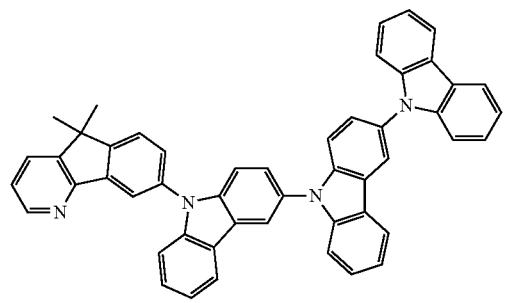
(34)
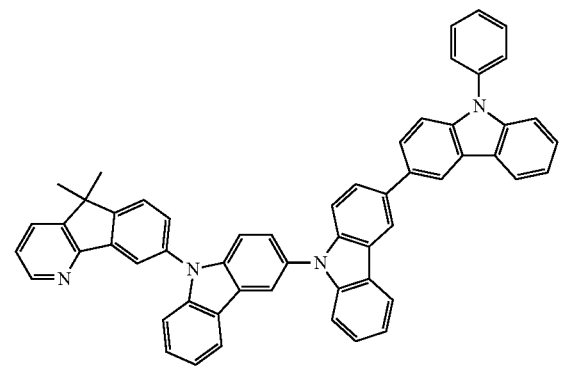
(35)
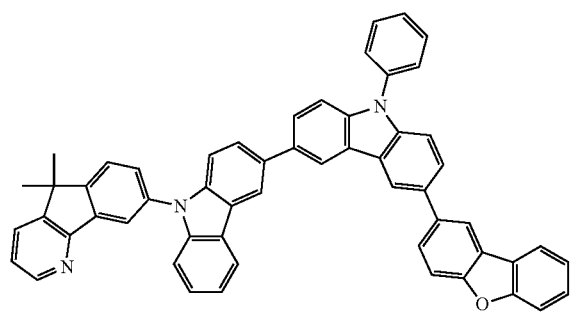
(36)
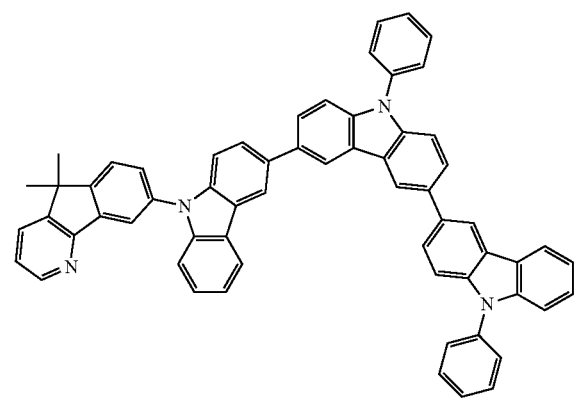

-continued
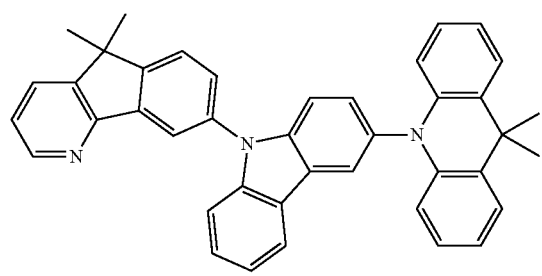
(37)
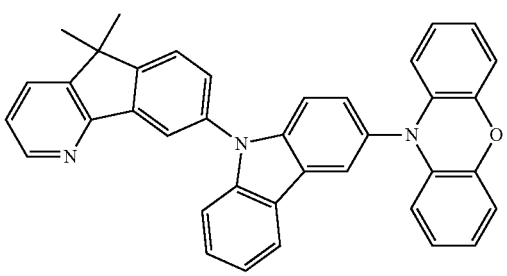
(38)
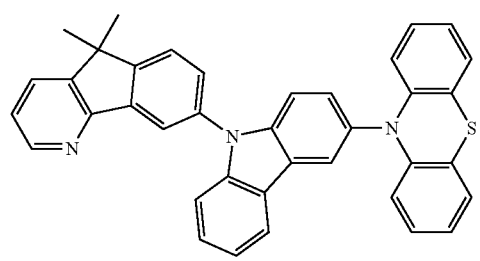
(39)
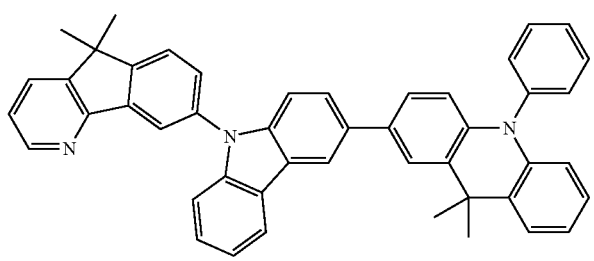
(40)
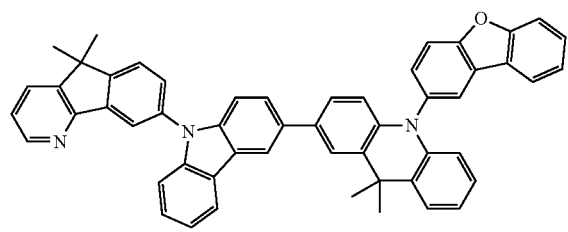
(41)
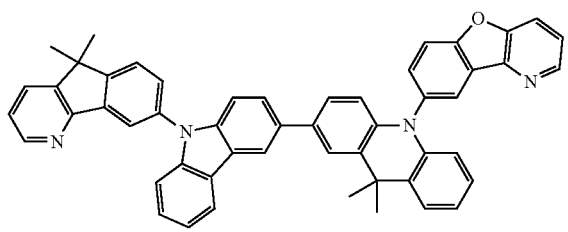
(42)
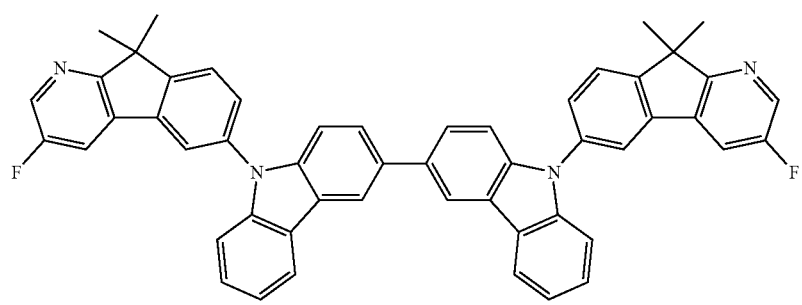
(43)
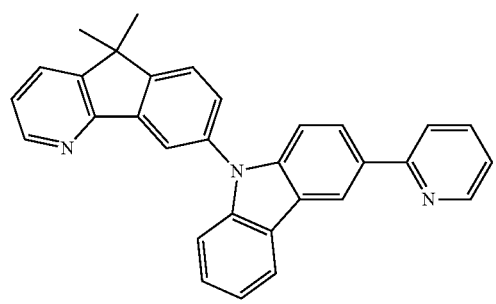
(44)
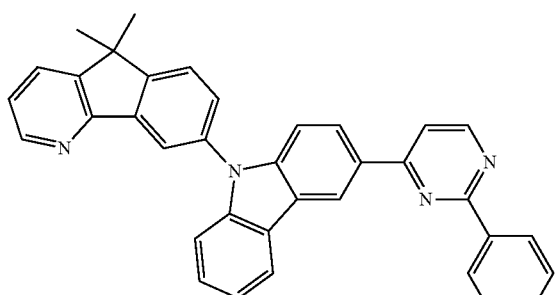
(45)

-continued
(46)
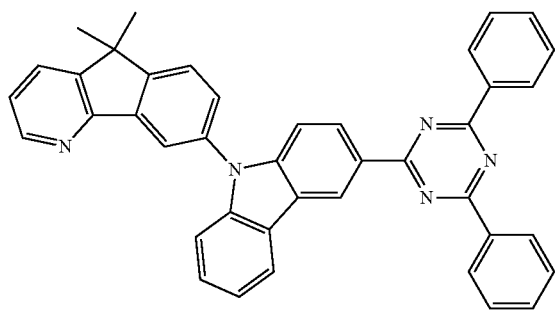
(47)
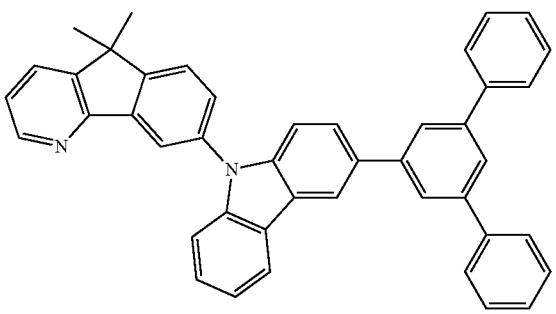
(48)
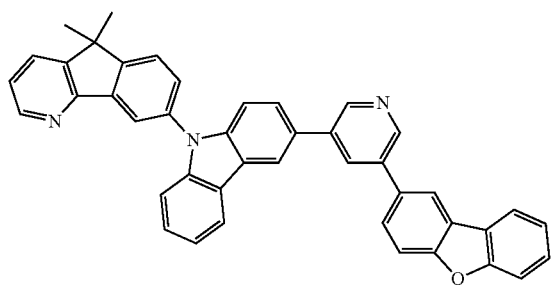
(49)
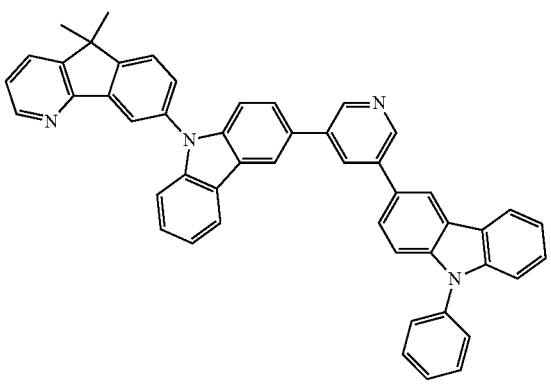
(50)
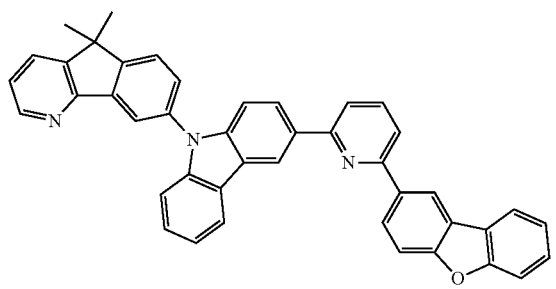
(51)
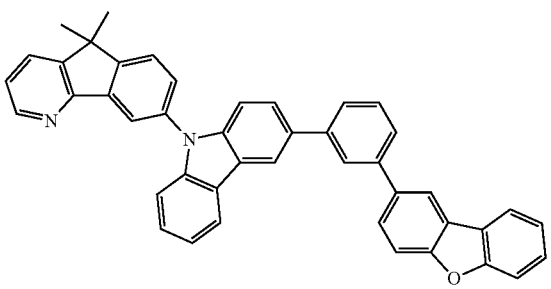
(52)
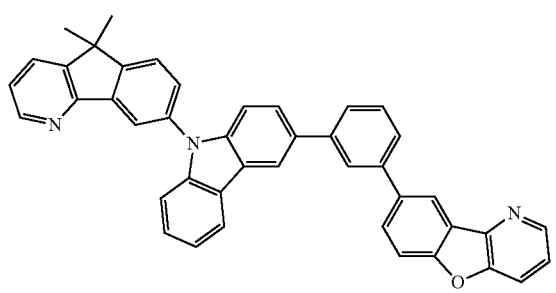
(53)
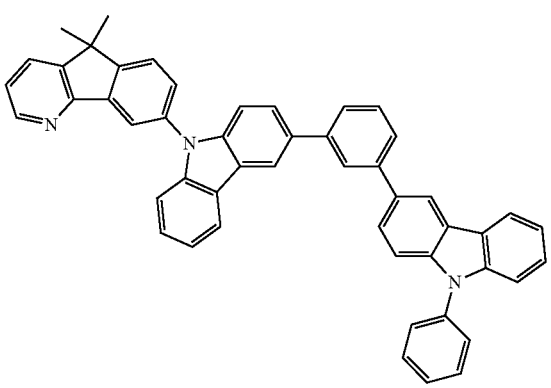

(54)
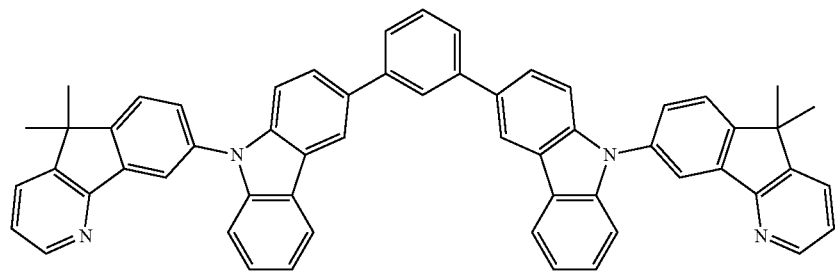
(55)
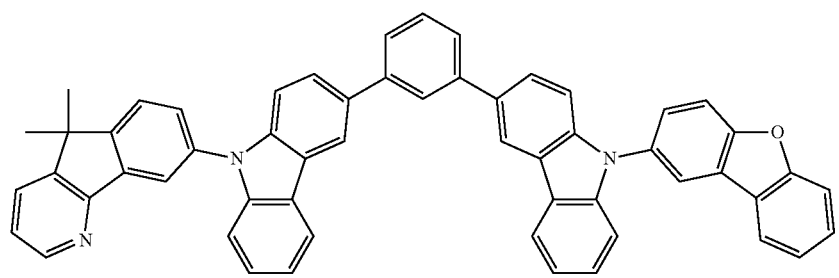
(56)
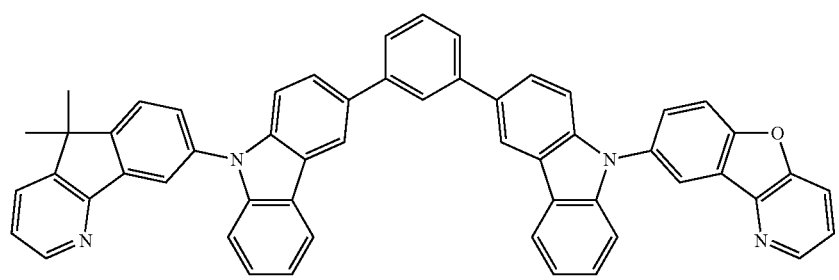
(57)
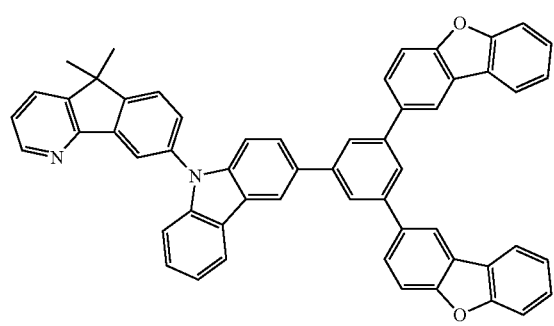
(58)
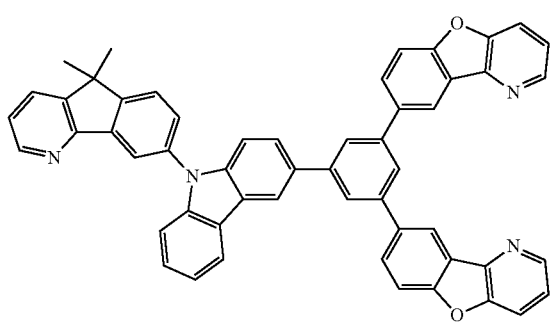

-continued
(59)
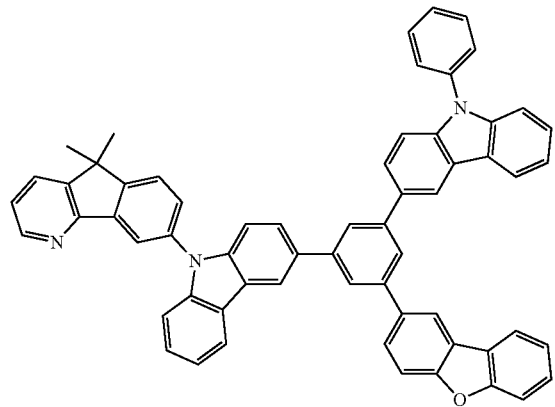
(60)
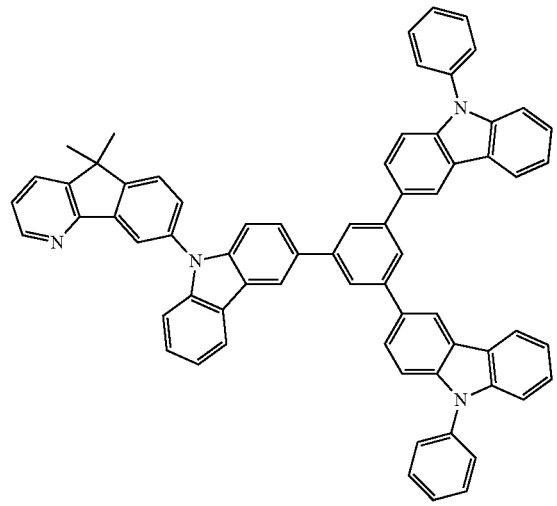
(61)
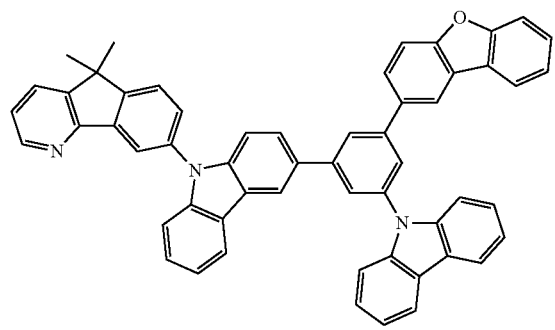
(62)
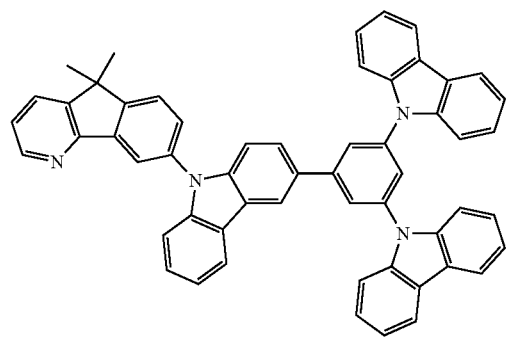
(63)
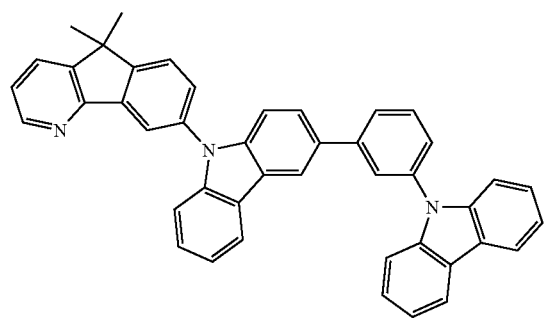
(64)
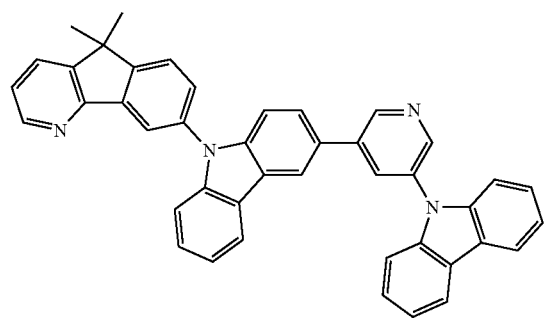
(65)
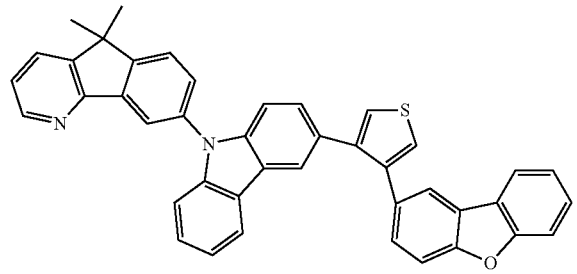
(66)
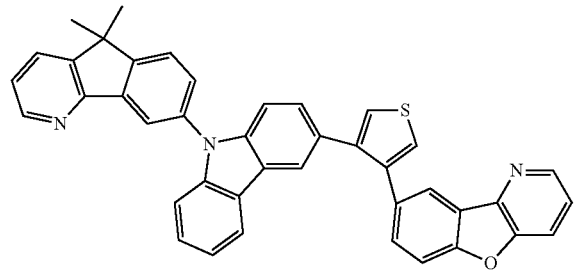

-continued
(67)
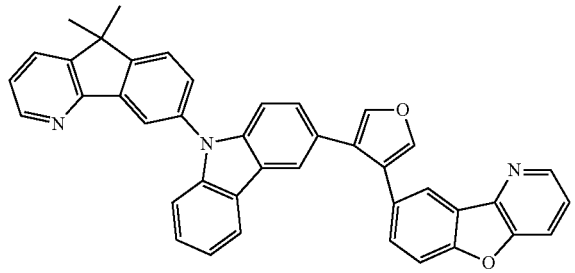
(68)
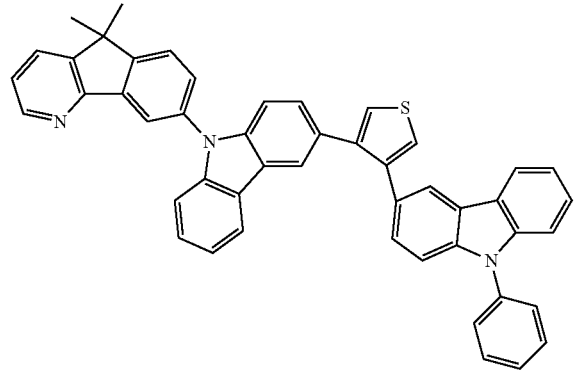
(69)
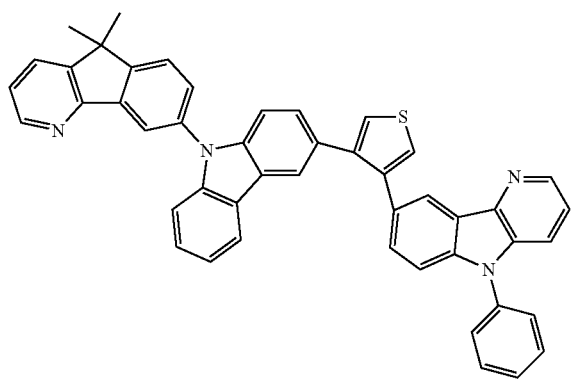
(70)
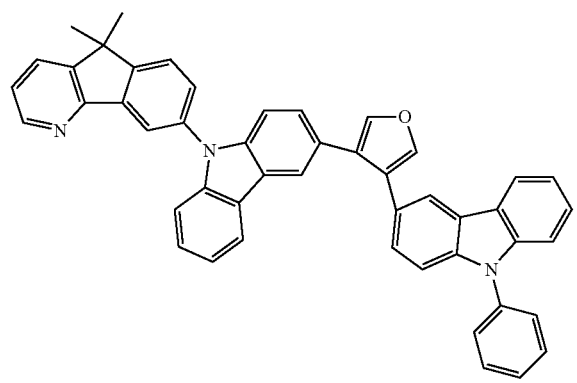
(71)
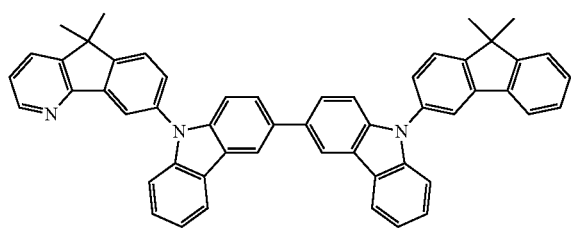
(72)
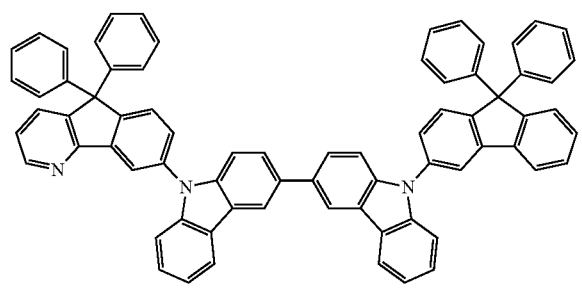
(73)
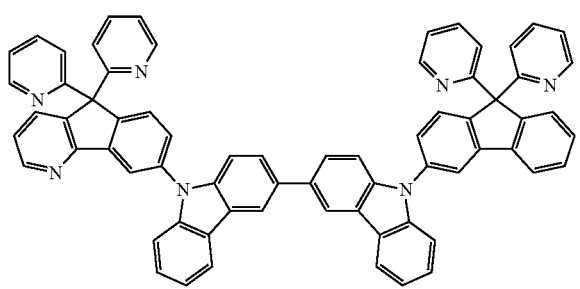
(74)
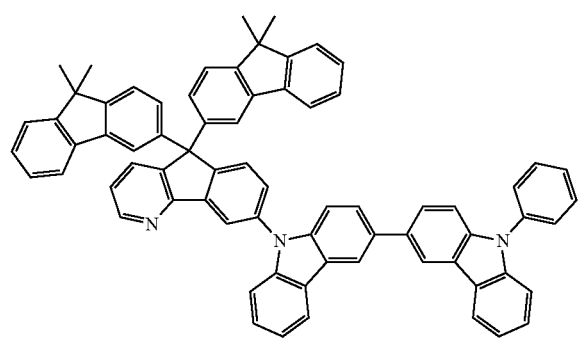

-continued

(75)
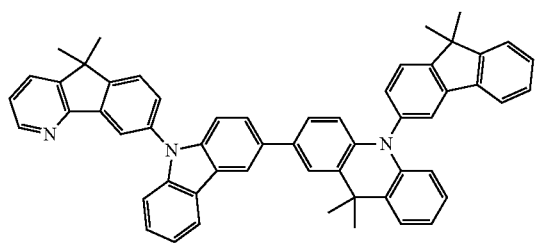

(76)
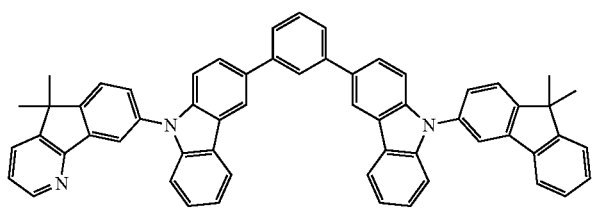

The compound represented by the formula (1) can be obtained by the following synthesis route, for example.

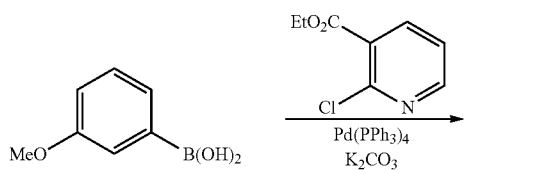 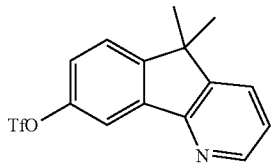

-continued

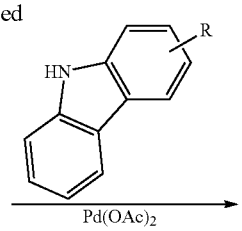

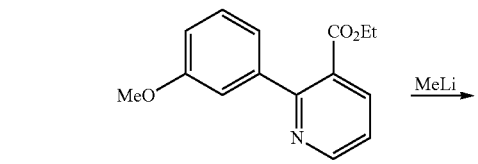 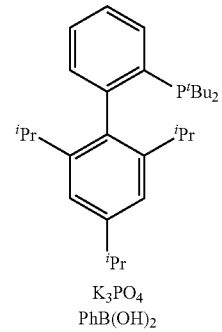

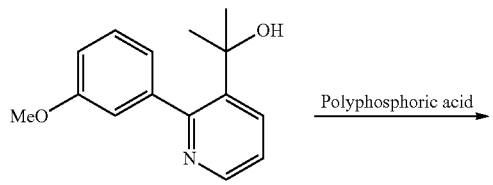 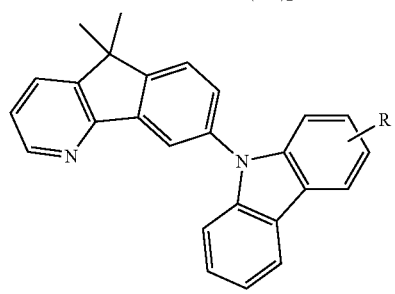

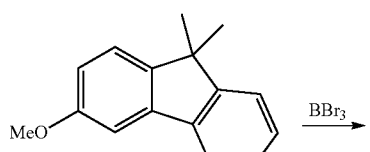

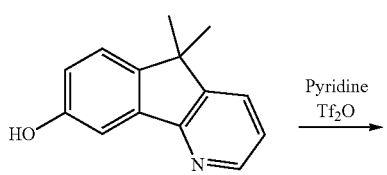

wherein R represents the same as $R_2$ in the formula (1).

The material for an organic electroluminescence device (organic EL device) of the invention (hereinafter, also referred to as the material of the invention) is characterized by containing the above-mentioned compound of the invention.

The material for an organic EL device of the invention can be suitably used as a material for an organic thin film layer constituting an organic EL device.

Subsequently, the organic EL device of the invention will be explained.

The organic EL device of the invention comprises one or more organic thin film layers including an emitting layer between an anode and a cathode. The material for an organic EL device of the invention is contained in at least one of the organic thin film layers.

In the organic EL device of the invention, it is preferred that the emitting layer contain the material for an organic EL device of the invention as a host material.

It is preferred that the emitting layer contain a phosphorescent emitting material, and the phosphorescent emitting material be an ortho-metalated complex of a metal atom selected from iridium (Ir), osmium (Os), and platinum (Pt).

In addition, in the organic EL device of the invention, it is preferred that an electron-transporting region be disposed between the cathode and the emitting layer, and the electron-transporting region comprise the material for an organic EL device of the invention.

It is preferred that an electron-injecting layer be disposed between the emitting layer and the cathode, and the electron-injecting layer comprise a nitrogen-containing ring derivative.

It is preferred that a hole-transporting region be disposed between the emitting layer and the anode, and the hole-transporting region comprise the above-mentioned material for an organic electroluminescence device.

FIG. 1 is a schematic view showing the layer construction according to one embodiment of the organic EL device of the invention.

The organic EL device 1 has a construction in which an anode 20, a hole-transporting region 30, a phosphorescent emitting layer 40, an electron-transporting region 50 and a cathode 60 are stacked on a substrate 10 in this order. The hole-transporting region 30 means a hole-transporting layer, a hole-injecting layer or the like. Similarly, the electron-transporting region 50 means an electron-transporting layer, an electron-injecting layer or the like. These layers may not be formed. It is preferred that one or more of these layers be formed. In this device, each organic layer provided in the hole-transporting region 30, the phosphorescent emitting layer 40 and each organic layer provided in the electron-transporting region 50 correspond to the above-mentioned organic thin film layers. Of these organic thin film layers, at least one layer contains the material for an organic EL device of the invention. Thereby, the resulting organic EL device can be driven at a low voltage.

Meanwhile, in the organic thin film layer containing the material for an organic EL device of the invention, the content of the material is preferably 1 to 100% by weight.

In the organic EL device of the invention, the material for an organic EL device of the invention is preferably contained in the phosphorescent emitting layer 40, and in particular, is preferably used as a host material in the emitting layer. Since the material of the invention has sufficiently large triplet energy, even if a blue phosphorescent dopant material is used, the triplet energy of the phosphorescent dopant material can be efficiently confined in the emitting layer. Meanwhile, the material of the invention can be used not only in a blue emitting layer but also in an emitting layer which emits light having a longer wave length (green to red or the like).

The phosphorescent emitting layer contains a phosphorescent emitting material (phosphorescent dopant). As the phosphorescent dopant, metal complex compounds can be given. Preferable is a compound having a metal atom selected from Ir, Pt, Os, Au, Cu, Re and Ru and a ligand. The ligand preferably has an ortho-metal bond.

In respect of a high phosphorescent quantum yield and capability of improving the external quantum efficiency of an emitting device, the phosphorescent dopant is preferably a compound having a metal atom selected from Ir, Os and Pt. Further preferable are a metal complex such as an iridium complex, an osmium complex and a platinum complex. Among them, an iridium complex and a platinum complex are more preferable, and an ortho-metalated iridium complex is most preferable. The dopant may be used singly or in combination of two or more.

The concentration of the phosphorescent dopant in the phosphorescent emitting layer is, but not particularly limited to, preferably 0.1 to 30% by weight, with 0.1 to 20% by weight being more preferable.

It is also preferred that the material of the invention be used in layers adjacent to the phosphorescent emitting layer 40. For example, in the device shown in FIG. 1, when a layer containing the material of the invention is formed between the hole-transporting region 30 and the phosphorescent emitting layer 40, (which is the layer adjacent to the emitting layer in the anode side), the layer can function as an electron-blocking layer and an exciton-barrier layer.

On the other hand, when a layer containing the material of the invention is formed between the phosphorescent emitting layer 40 and the electron-transporting region 50, (which is the layer adjacent to the emitting layer in the cathode side), the layer can function as a hole-blocking layer and an exciton-barrier layer.

Meanwhile, the blocking (barrier) layer is the layer which blocks transporting of carriers or diffusion of excitons. The organic layer which prevents electrons from leaking from an emitting layer into a hole-transporting region is mainly defined as an electron-blocking layer. The organic layer which prevents holes from leaking from an emitting layer into an electron-transporting region is often defined as a hole-blocking layer. In addition, the organic layer which prevents triplet excitons generated in an emitting layer from diffusing to the peripheral layers having lower triplet energy than that of the emitting layer is often defined as an exciton-barrier layer (triplet-blocking layer).

Moreover, it is also possible to use the material of the invention in the layers adjacent to the phosphorescent emitting layer 40, and further in other organic thin film layers which bond to the adjacent layers.

In addition, when two or more emitting layers are formed, the material of the invention can be suitably used in a spacing layer formed between the emitting layers.

Figure 2:
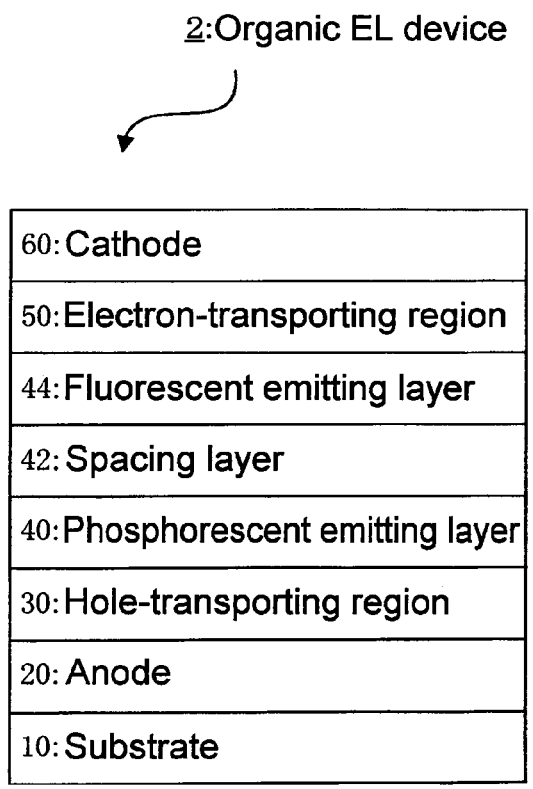
FIG. 2 is a schematic view showing the layer construction according to another embodiment of the organic EL device of the invention.

FIG. 2 is a schematic view showing the layer construction according to another embodiment of the organic EL device of the invention.

The organic EL device 2 is an example of a hybrid-type organic EL device in which a phosphorescent emitting layer and a fluorescent emitting layer are stacked.

The organic EL device 2 has the same construction as the above-mentioned organic EL device 1, except that a spacing layer 42 and a fluorescent emitting layer 44 are formed between a phosphorescent emitting layer 40 and an electron-transporting region 50. In the construction in which the phosphorescent emitting layer 40 and the fluorescent emitting layer 44 are stacked, for preventing excitons generated in the phosphorescent emitting layer 40 from diffusing into the fluorescent emitting layer 44, the spacing layer 42 may be provided between the fluorescent emitting layer 44 and the phosphorescent emitting layer 40. Since the material of the invention has a large triplet energy, it can function as a spacing layer.

In the organic EL device 2, for example, by allowing the phosphorescent emitting layer to emit yellow light and by allowing the fluorescent emitting layer to emit blue light, an organic EL device which emits white light can be obtained. Meanwhile, in this embodiment, the phosphorescent emitting layer and the fluorescent emitting layer are each formed as a single layer. However, the configuration is not limited thereto, and they may be each formed as two or more layers.

Their manner of formation can be selected appropriately depending on the intended use such as lightning or a display device. For example, when a full-color emitting device is realized by utilizing a white emitting device and color filters, the phosphorescent emitting layer and the fluorescent emitting layer preferably include emissions in the plural wave length regions such as red, green and blue (RGB), or red, green, blue and yellow (RGBY) in respect of color rendering properties.

In addition to the above-mentioned embodiments, the organic EL device of the invention can employ various known structures. Further, the emission from an emitting layer can be outcoupled from the anode side, the cathode side or the both sides.

In the organic EL device of the invention, the constitution of layers other than those using the above-mentioned material of an organic EL device of the invention is not particularly limited. As the constitution of the layers, known materials and the like can be used. Hereinafter, the layers of the device according to the embodiment 1 will be briefly explained. However, the materials applied to the organic EL device of the invention are not limited to the following.

(Substrate)

As the substrate, a glass plate, a polymer plate or the like can be used.

As the glass plate, particularly, soda-lime glass, barium/strontium-containing glass, lead glass, aluminosilicate glass, borosilicate glass, barium borosilicate glass, quartz or the like can be given. As the polymer plate, polycarbonate, acrylic resin, polyethylene terephthalate, polyethersulfone, polysulfone or the like can be given.

(Anode)

The anode is formed of a conductive material, for example. A conductive material having a work function larger than 4 eV is suitable.

Examples of the above-mentioned conductive material include carbon, aluminum, vanadium, iron, cobalt, nickel, tungsten, silver, gold, platinum, palladium or the like and alloys thereof, a metal oxide such as tin oxide or indium oxide used in ITO substrate or NESA substrate, and an organic conductive resin such as polythiophene and polypyrrole.

The anode can be formed in the form of two or more layers if needed.

(Cathode)

The cathode is formed of a conductive material, for example. A conductive material having a work function smaller than 4 eV is suitable.

Examples of the above-mentioned conductive material include magnesium, calcium, tin, lead, titanium, yttrium, lithium, ruthenium, manganese, aluminum, lithium fluoride or the like, and alloys thereof, but not limited thereto.

Further, representative examples of the above-mentioned alloys include magnesium/silver, magnesium/indium, lithium/aluminum, but not limited thereto. The ratio of the alloy can be selected appropriately by controlling the temperature of a deposition source, the atmosphere, the vacuum level or the like.

The cathode may be formed in the form of two or more layers if needed. The cathode can be prepared by forming a thin film of the above-mentioned conductive material by deposition, sputtering or the like.

When emission from an emitting layer is outcoupled through a cathode, it is preferred that the transmittance for emission of the cathode be larger than 10%.

In addition, the sheet resistance as a cathode is preferably several hundred $\Omega/\square$ or less. The thickness is normally 10 nm to 1 µm, with 50 to 200 nm being preferable.

(Emitting Layer)

When a phosphorescent emitting layer is formed by using materials other than the material for an organic EL device of the invention, materials which are known as a material for a phosphorescent emitting layer can be used. Specifically, reference can be made to WO2005/079118 or the like.

The organic EL device of the invention may comprise a fluorescent emitting layer as the device shown in FIG. 2. For the fluorescent emitting layer, known materials can be used.

The emitting layer can be a double-host (often referred to as host/co-host) type. Specifically, in the emitting layer, an electron-transporting host and a hole-transporting host may be combined to control the carrier balance.

The emitting layer also can be of a double-dopant type. By incorporating two or more kinds of dopant materials having a high quantum yield to the emitting layer, each dopant emits. For example, there may be a case that a yellow emitting layer is realized by co-depositing a host, and a red dopant and a green dopant.

The emitting layer may be a single layer, or have a stacked structure. When the emitting layer has a stacked structure, due to the accumulation of electrons and holes in the interface of the emitting layers, the recombination region can be concentrated in the interface of the emitting layers, thereby increasing the quantum efficiency.

(Hole-Injecting Layer and Hole-Transporting Layer)

The hole-injecting/transporting layer helps holes to be injected to an emitting layer and transports the injected holes to an emitting region. It has a large hole mobility and normally a small ionization energy of 5.6 eV or less.

As the material for a hole-injecting/transporting layer, materials which can transport holes to an emitting layer at a lower electric field intensity are preferable. In addition, it is preferred that the hole mobility be at least $10^{-4}$ cm$^2$/V·second when an electric field intensity of $10^4$ to $10^6$ V/cm is applied, for example.

Specific examples of materials for a hole-injecting/transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712, 47-25336 and 54-119925, and others), arylamine derivatives (see U.S. Pat. Nos. 3,567,450, 3,240,597, 3,658, 520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257, 203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), and aniline copolymers (JP-A-2-282263).

Also, an inorganic compound such as p-type Si and p-type SiC can be used as the hole-injecting material.

As the material for a hole-injecting/transporting layer, a cross-linking material can be used. As the cross-linking hole-injecting/transporting layer, a layer formed of the cross-linking material disclosed in Chem. Mater. 2008, 20, 413-422, Chem. Mater. 2011, 23(3), 658-681, WO2008108430, WO2009102027, WO2009123269, WO2010016555, WO2010018813 or the like insolubilized by heat, light or the like can be given, for example.

(Electron-Injecting Layer and Electron-Transporting Layer)

The electron-injecting/transporting layer helps electrons to be injected to an emitting layer and transports the injected electrons to an emitting region. It has a large electron mobility.

In the organic EL device, it is known that since emitting light is reflected by an electrode (a cathode, for example), emission outcoupled directly from an anode interferes with emission after being reflected by the electrode. In order to utilize the interference effect efficiently, the film thickness of the electron injecting/transporting layer is appropriately selected to be several nm to several μm. When the film thickness is particularly large, it is preferred that the electron mobility be at least $10^{-5}$ cm$^2$/V·s or more at an applied electric field intensity of $10^4$ to $10^6$ V/cm in order to avoid an increase in voltage.

As the electron-transporting material used in the electron-injecting/transporting layer, an aromatic hetero ring compound containing one or more hetero atoms in the molecule is preferably used, with a nitrogen-containing ring derivative being particularly preferable. Further, as the nitrogen-containing ring derivative, an aromatic ring having a nitrogen-containing six-membered ring or five-membered ring skeleton, or a fused aromatic ring compound having a nitrogen-containing six-membered ring or five-membered ring skeleton is preferable. Examples thereof include compounds containing a pyridine ring, a pyrimidine ring, a triazine ring, a benzimidazole ring, a phenanthroline ring, a quinazoline ring or the like in the skeleton.

In addition, an organic layer with a semiconductor property may be formed by doping a donor material (n) or doping an acceptor material (p). Representative examples of N-doping include doping of an electron-transporting material with a metal such as Li or Cs. Representative examples of P-doping include doping of a hole-transporting material with an acceptor material such as F4TCNQ (see Japan Patent No. 3695714, for example).

The organic EL device of the invention preferably comprises at least one of an electron-donating dopant and an organic metal complex in the interface region between a cathode and an organic thin film layer.

By this structure, the organic EL device can have an improved luminance and a prolonged life.

As the electron-donating dopant, at least one selected from an alkali metal, an alkali metal compound, an alkaline-earth metal, an alkaline-earth metal compound, a rare-earth metal and a rare-earth metal compound can be given.

As the organic metal complex, at least one selected from an organic metal complex including an alkali metal, an organic metal complex including an alkaline-earth metal and an organic metal complex including a rare-earth metal can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) and the like can be given. One having a work function of 2.9 eV or less is particularly preferable. Of these, K, Rb and Cs are preferable, Rb or Cs is further preferable, and Cs is most preferable.

As the alkaline-earth metal, calcium (Ca) (work function: 2.9 eV), strontium (Sr) (work function: 2.0 eV or more and 2.5 eV or less), barium (Ba) (work function: 2.52 eV) and the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

The preferable metals of the above-mentioned metals have a particularly high reducing ability, and hence can provide the resulting organic EL device with an improved luminance and a prolonged life by adding a relative small amount of the metal to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Of these, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium oxide ($Ba_xSr_{1-x}O$) ($0<x<1$) and barium calcium oxide ($Ba_xCa_{1-x}O$) ($0<x<1$). Of these, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Of these, $YbF_3$, $ScF_3$ and $TbF_3$ are preferable.

The organic metal complexes are not particularly limited as long as the complexes each contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

For the addition form of the electron-donating dopant and the organic metal complex, it is preferred that the electron-donating dopant and the organic metal complex be formed in a shape of a layer or an island in the interfacial region. A preferred method for the formation is a method in which while at least one of the electron-donating dopant and the organic metal complex is deposited by a resistant heating deposition method, an organic substance as a light emitting material or an electron-injecting material for forming the interfacial region is deposited at the same time, thereby dispersing at least one of the electron-donating dopant and the organic metal complex reducing dopant in the organic substance. The disperse concentration by molar ratio of the organic substance to the electron-donating dopant and/or the organic metal complex is normally 100:1 to 1:100, preferably 5:1 to 1:5.

In a case where at least one of the electron-donating dopant and the organic metal complex is formed into the shape of a layer, the light emitting material or electron injecting material which serves as an organic layer in the interface is formed into the shape of a layer. After that, at least one of the electron-donating dopant and the organic metal complex is solely deposited by the resistant heating deposition method to form a layer preferably having a thickness of 0.1 nm or more and 15 nm or less.

In a case where at least one of the electron-donating dopant and the organic metal complex is formed into the shape of an island, the light emitting material or the electron injecting material which serves as an organic layer in the interface is formed into the shape of an island. After that, at least one of the electron-donating dopant and the organic metal complex is solely deposited by the resistant heating deposition method to form an island preferably having a thickness of 0.05 nm or more and 1 nm or less.

In addition, the ratio of the main component (the emitting material or the electron-injecting material) to at least one of the electron-donating dopant and the organic metal complex in the organic EL device of the invention is preferably 5:1 to 1:5, more preferably 2:1 to 1:2 in terms of a molar ratio.

Each layer of the organic EL device of the invention can be formed by using known methods including the dry-type film formation such as vacuum deposition, sputtering, plasma ion-plating or the like and the wet-type film formation such as spin coating, dipping, flow coating or the like.

The film thickness of each layer is not particularly limited, but is required to be set to be a proper thickness. If the film thickness is too large, a large applied voltage is required in order to obtain the predetermined light output, thereby leading to low efficiency. If the film thickness is too small, due to generation of pinholes or the like, sufficient luminance cannot be obtained when an electric field is applied. Normally, the film thickness is preferably 5 nm to 10 μm, and the range of 10 nm to 0.2 μm is further preferable.

EXAMPLES

Material for Organic Electroluminescence Device

Synthesis Example 1

Synthesis of Compound (1)

The following compound (1) was synthesized.

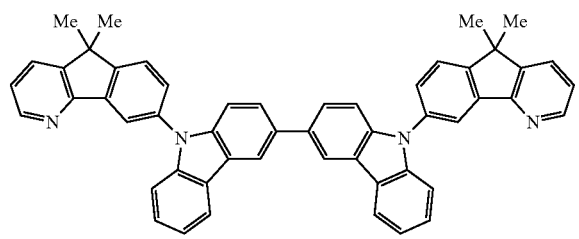

(1)

(1) Synthesis of Intermediate (1-a)

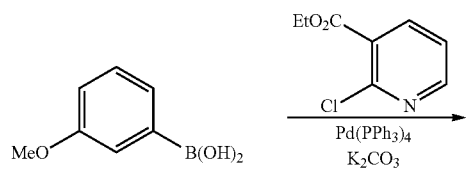

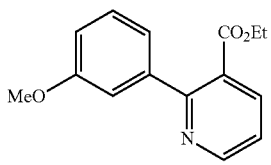

(1-a)

Under a nitrogen atmosphere, 15.20 g (100 mmol) of 3-methoxyphenyl boronic acid, 18.56 g (100 mmol) of ethyl 2-chloro nicotinate, 2.31 g (2.00 mmol) of tetrakis(triphenylphosphine)palladium, 150 mL of 1,4-dioxane and 150 mL of a 2M aqueous solution of potassium carbonate were placed in a three neck flask, and refluxed for 8 hours. After completion of the reaction, the resulting mixture was cooled to room temperature, and then subjected to extraction with dichloromethane by means of a separating funnel and dried with anhydrous magnesium sulfate, followed by filtration and concentration. The crude product obtained was purified by a using silica gel column to obtain a yellow oily matter (intermediate (1-a)). The yield was 25.72 g and the percent yield was 100%.

(2) Synthesis of Intermediate (1-b)

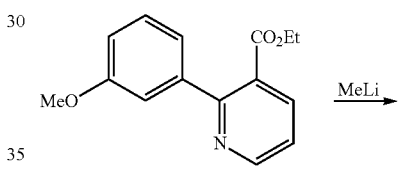

(1-a)

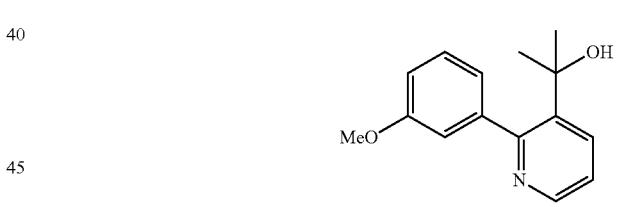

(1-b)

Under a nitrogen atmosphere, 25.72 g (100 mmol) of intermediate (1-a) and 120 mL of dehydrated tetrahydrofuran were placed in a three neck flask, and cooled to −78° C. To the resulting solution, 263.2 mL (1.14M in diethylether, 300 mmol) of methyllithium was added dropwise for 10 minutes. After stirred at −78° C. for 20 minutes, the resulting mixture was heated to room temperature, and then stirred at room temperature for 24 hours. After completion of the reaction, 50 mL of water was added. The mixture was subjected to extraction with ethyl acetate by using a separating funnel, and dried with anhydrous magnesium sulfate, followed by filtration and concentration. The crude product obtained was purified by using a silica gel column to obtain yellow solids (intermediate (1-b)). The yield was 14.81 g and the percent yield was 61%.

(3) Synthesis of Intermediate (1-c)

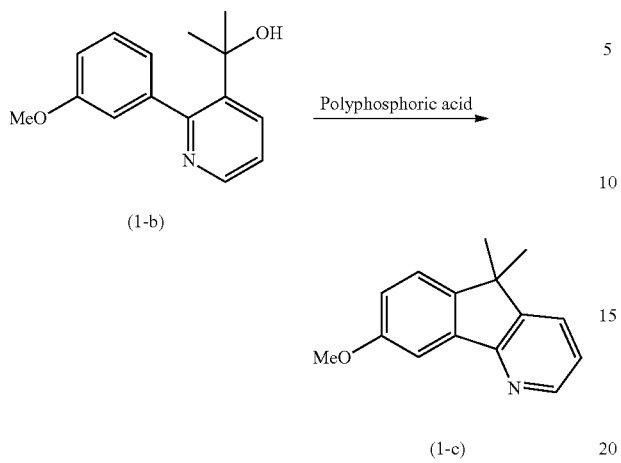

Under a nitrogen atmosphere, 13.60 g (55.9 mmol) of intermediate (1-b) and 100 g of polyphosphoric acid were placed in a three neck flask, and stirred at 70° C. for 48 hours. After a completion of the reaction, the mixture was cooled to room temperature and ice was added. The mixture was neutralized in a saturated aqueous solution of sodium hydrocarbon. The resulting solution was subjected to extraction with dichloromethane by using a separating funnel and dried with anhydrous magnesium sulfate, followed by filtration and concentration. The crude product obtained was purified by using a silica gel column to obtain an oily yellow matter (intermediate (1-c)). The yield was 7.34 g and the percent yield was 58%.

(4) Synthesis of Intermediate (1-d)

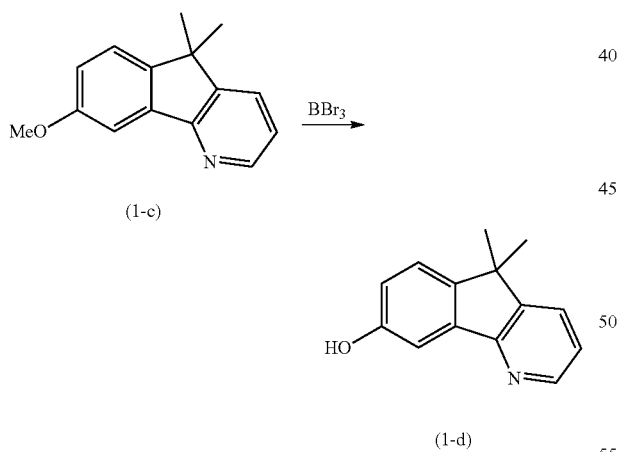

Under a nitrogen atmosphere, 7.34 g (32.6 mmol) of intermediate (1-c) and 160 mL of dichloromethane were placed in a three neck flask, and cooled to 0° C. To the resulting solution, 32.6 mL (1M in dichloromethane, 32.6 mmol) of boron tribromide was added dropwise for 10 minutes. After stirred at 0° C. for 20 minutes, the resulting mixture was heated to room temperature, and then stirred at room temperature for 19 hours. After a completion of the reaction, the resultant was cooled to 0° C., and 50 mL of water was added. The mixture was subjected to extraction with dichloromethane by using a separating funnel, and dried with anhydrous magnesium sulfate, followed by filtration and concentration. The crude product obtained was purified by using a silica gel column to obtain white solids (intermediate (1-d)). The yield was 6.20 g and the percent yield was 90%.

(5) Synthesis of Intermediate (1-e)

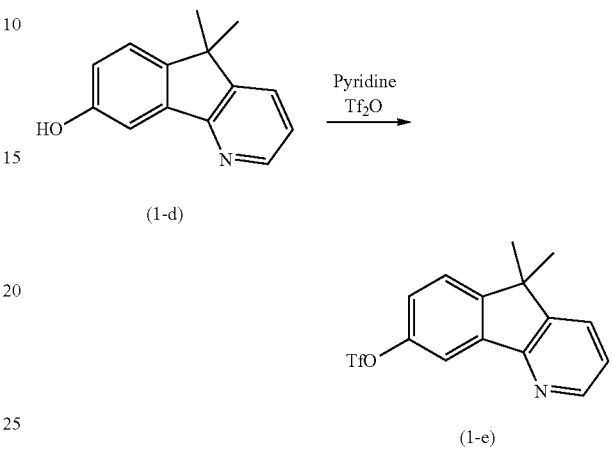

Under a nitrogen atmosphere, 6.20 g (29.3 mmol) of intermediate (1-d), 4.64 g (58.6 mmol) of pyridine and 80 mL of dichloromethane were placed in a three neck flask, and cooled to 0° C. To the resulting solution, 5.92 mL of trifluoromethanesulfonic anhydride was added dropwise for 10 minutes. After stirred at 0° C. for 20 minutes, the resulting mixture was heated to room temperature, and then stirred at room temperature for 8 hours. After completion of the reaction, the resulting solution was cooled to 0° C., followed by addition of 50 mL of 10% hydrochloric acid. The mixture was subjected to extraction with dichloromethane by using a separating funnel. The extracted matter was washed with a saturated aqueous solution of sodium hydrogen carbonate, and dried with anhydrous magnesium sulfate, followed by filtration and concentration. The crude product obtained was purified by using silica gel column to obtain white solids (intermediate (1-e)). The yield was 9.10 g and the percent yield was 89%.

(6) Synthesis of Compound (1)

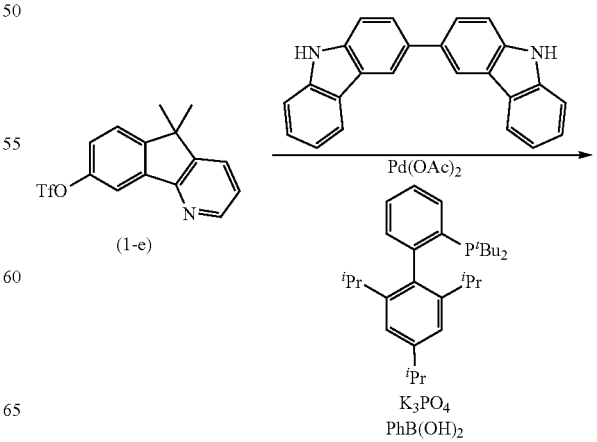

-continued

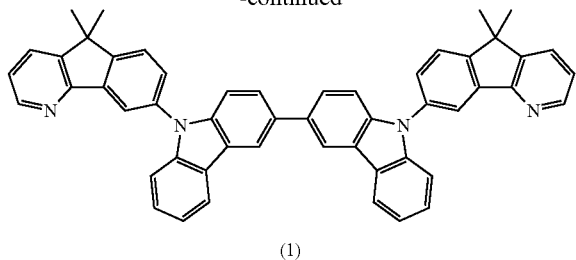

(1)

Under a nitrogen atmosphere, 8.82 g (25.7 mmol) of intermediate (1-e), 3.41 g (10.3 mmol) of 3,3'-bis(9H-carbazole), 0.23 g (1.03 mmol) of palladium acetate, 1.09 g (2.57 mmol) of 2-di-t-butylphosphino-2',4',6'-triisopropyl biphenyl, 10.90 g (51.4 mmol) of potassium phosphate, 0.13 g (1.03 mmol) of phenylboronic acid, 20 mL of toluene and 40 mL of t-butanol were placed in a three neck flask, and refluxed at 110° C. for 15 hours. After completion of the reaction, the resulting mixture was cooled to room temperature, and then subjected to extraction with dichloromethane by means of a separating funnel and dried with anhydrous magnesium sulfate, followed by filtration and concentration. The crude product obtained was purified by using a silica gel column to obtain white solids (compound (1)) (yield: 4.80 g, percent yield: 65%). By field desorption mass spectrometry, the white solids obtained was identified to compound (1).

Example 1

A glass substrate with ITO electrode lines having a film thickness of 130 nm (manufactured by Geomatics Co.) was subjected to ultrasonic cleaning in isopropyl alcohol for 5 minutes and then UV ozone cleaning for 30 minutes.

The cleaned glass substrate with transparent electrode lines was mounted on a substrate holder in a vacuum deposition apparatus. The following compound (HI1) was deposited by resistance heating on the surface of the glass substrate on which the transparent electrode lines had been formed such that the ITO electrode lines were covered to form a 20 nm-thick film, and subsequently the following compound (HT1) to form a 60 nm-thick film. The films were formed at a deposition rate of 1 Å/s. These thin films served as a hole-injecting layer and a hole-transporting layer, respectively.

Next, on the hole-transporting layer, the following compound (H1) and the following compound (BD1) were simultaneously deposited by resistance heating to form a 50 nm-thick film. Then compound (BD1) was deposited such that the mass ratio of compound (BD1) relative to the total mass of compound (H1) and compound (BD1) become 20%. The film formation rates were set to be 1.2 Å/s and 0.3 Å/s, respectively. This thin film served as a phosphorescent emitting layer.

Next, on the phosphorescent emitting layer, the compound (1) obtained in synthesis example 1 was deposited by resistance heating to form a 10 nm-thick thin film. The film formation rate was 1.2 Å/s. This thin film served as a blocking layer.

Subsequently, on the blocking layer, the following compound (ET1) was deposited by resistance heating to form a 10 nm-thick thin film. The film formation rate was 1 Å/s. This thin film served as an electron-injecting layer.

Next, on the electron-injecting layer, LiF was deposited at a film formation rate of 0.1 Å/s to form a 1.0 nm-thick thin film.

Subsequently, on this LiF film, metal aluminum was deposited at a film formation rate of 8.0 Å/s to form a 80 nm-thick metal electrode, whereby an organic EL device was obtained.

Compound (HI1)

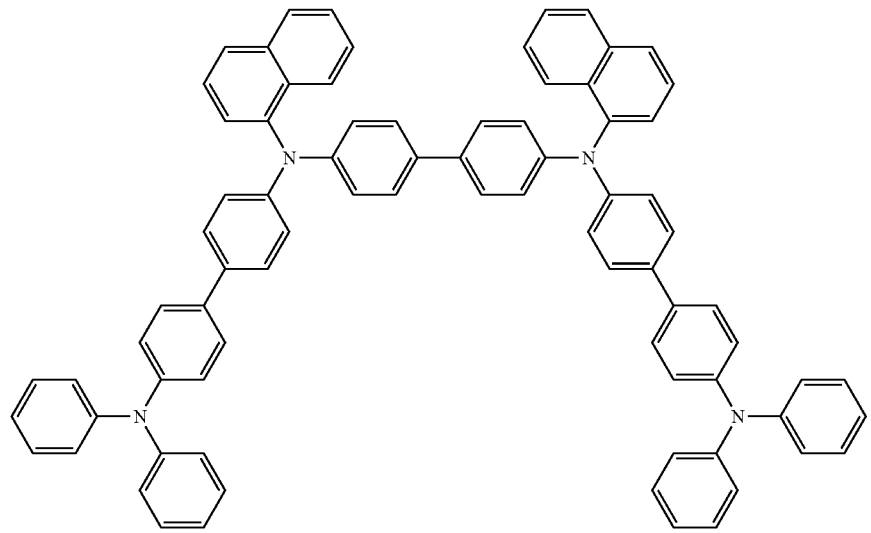

-continued

Compound (HT1)

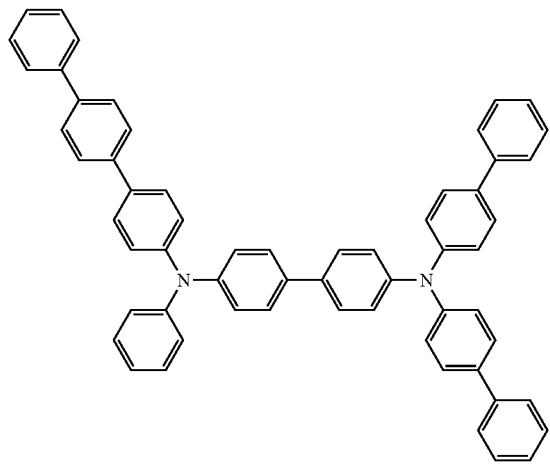

Compound (H1)

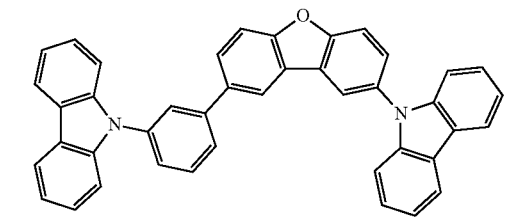

Compound (BD1)

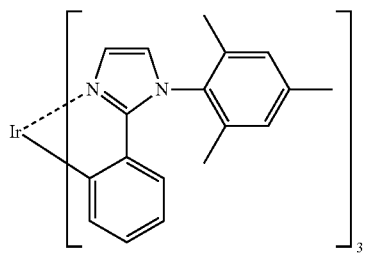

Compound (ET1)

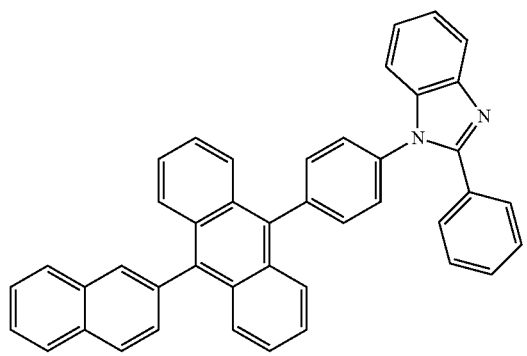

The organic EL device produced was evaluated for the following items. Table 1 shows the results.

(1) External Quantum Efficiency (%)

At 23° C., under dried nitrogen gas atmosphere, the external quantum efficiency at a luminance of 1000 cd/m² was measured by using a luminous meter (spectral radiance meter CS-1000 manufactured by Konica Minolta, Inc.).

(2) Half Life (Hours)

A continuous current (direct current) test was conducted at an initial luminance of 1000 cd/m². The time taken for the luminance to decrease by half was determined.

(3) Voltage (V)

At 23° C., under dried nitrogen gas atmosphere, using KEITHLY 236 SOURCE MEASURE UNIT, a voltage was applied to a device which has been electrically-wired, thereby to allow the device to emit. The voltage applied to the wiring resistance other the device was deducted from the entire applied voltage, whereby the voltage applied to the device was determined. At the same time of applying voltage and measurement, luminous measurement was conducted by using a luminous meter (spectral radiance meter CS-1000 manufactured by Konica Minolta, Inc.). From these measurement results, the voltage at a device luminance of 100 cd/m² was read.

TABLE 1

| | Blocking layer | Voltage (V) | External quantum efficiency (%) | Luminance Half life (hours) |
|---|---|---|---|---|
| Example 1 | Compound (1) | 4.8 | 17.5 | 7300 |

Table 2 shows the triplet energies of the materials for an organic EL device used in Examples. The triplet energy is defined as follows. A sample is dissolved in an EPA solvent (diethyl ether: isopentane: ethanol=5:5:2 (volume ratio)) at the ratio of 10 μmol/L to obtain a sample for phosphorescent measurement. The sample for phosphorescent measurement is put in a quartz cell. The quartz cell is irradiated with excited light at a temperature of 77K. The radiated phosphorescent spectrum is measured. The triplet energy is determined from the measured spectrum by converting with the expression: $E'(ev)=1239.85/\lambda_{edge}$.

TABLE 2

| Compound | Triplet energy (eV) |
|---|---|
| Compound (1) | 2.91 |
| Compound (BD1) | 2.64 |

From Table 1, it is found that the organic EL device using the material for an organic EL device of the invention has a long life, a high efficiency, and can be driven at a low voltage.

Moreover, from Table 2, it is found that the material for an organic EL device of the invention has a high triplet energy, which can be used as a blocking layer material for a blue phosphorescence-emitting EL device.

INDUSTRIAL APPLICABILITY

The organic EL device of the invention can be utilized for a planar emitting body such as a flat panel display of a wall-hanging television, a copier, a printer, a back light of a liquid crystal display, or a light source in instruments or the like, a sign board, a signal light or the like.

The material for an organic EL device of the invention can be used for an organic EL device, an organic EL display, lightnings, an organic semiconductor, an organic solar cell or the like.

The material for an organic EL device of the invention is useful for realizing an organic EL device which can be driven at a low voltage with a high efficiency and a prolonged life.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in this specification and the Japanese application specification claiming priority under the Paris Convention are incorporated herein by reference in its entirety.

The invention claimed is:

1. A compound represented by the following formula (1):

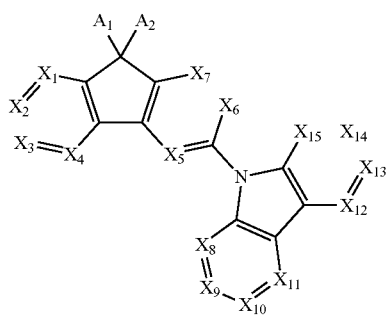

(1)

wherein $X_1$ to $X_7$ are independently a nitrogen atom, or a carbon atom that $R_1$ is bonded to, provided that at least one of $X_1$ to $X_7$ is a nitrogen atom;

$R_1$ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted silyl group, or a fluoro group, and when two or more $R_1$s are present in the formula (1), $R_1$s may be the same or different from each other;

$X_8$ to $X_{15}$ are independently a nitrogen atom, or a carbon atom that $R_2$ is bonded to;

$R_2$ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, and when two or more $R_2$s are present in the formula (1), $R_2$s may be the same or different from each other; and $A_1$ and $A_2$ are independently a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

2. The compound according to claim 1, which is a compound represented by the following formula (2):

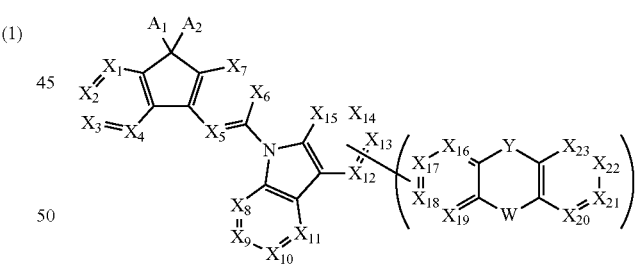

(2)

wherein $X_1$ to $X_{15}$, $A_1$ and $A_2$ independently represent the same as in the formula (1);

$X_{16}$ to $X_{23}$ are independently a nitrogen atom, or a carbon atom that $R_3$ is bonded to;

$R_3$ represents a hydrogen atom, a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, and when two or more $R_3$s are present in the formula (2), $R_3$s may be the same or different from each other;

Y represents an oxygen atom (O), a sulfur atom (S) or $NR_4$;

$R_4$ represents a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group;

W represents a single bond, O, S, $P(R_5)$, $P(=O)(R_6)$, $N(R_7)$, $Si(R_8)(R_9)$ or $C(R_{10})(R_{11})$; and $R_5$ to $R_{11}$ independently represent a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group, provided that one carbon atom selected from $X_{12}$ to $X_{15}$ is bonded through a single bond to one carbon atom selected from $X_{16}$ to $X_{19}$ or a nitrogen atom when Y is $NR_4$.

3. The compound according to claim 2, which is a compound represented by the following formula (3):

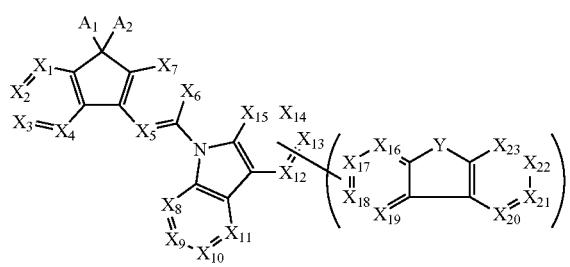

(3)

wherein $X_1$ to $X_{23}$, $A_1$, $A_2$ and Y independently represent the same as in the formula (2).

4. The compound according to claim 2, which is a compound represented by the following formula (4):

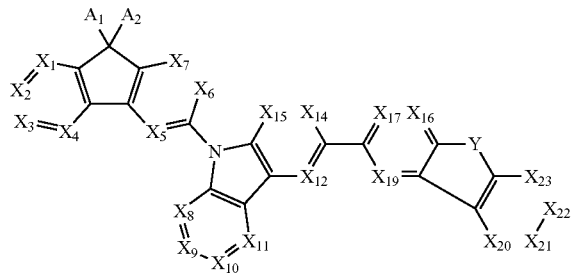

(4)

wherein $X_1$ to $X_{12}$, $X_{14}$ to $X_{17}$, $X_{19}$ to $X_{23}$, $A_1$, $A_2$ and Y independently represent the same as in the formula (2).

5. The compound according to claim 2, which is a compound represented by the following formula (5):

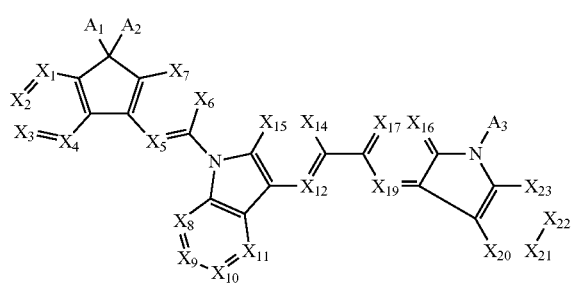

(5)

wherein $X_1$ to $X_{12}$, $X_{14}$ to $X_{17}$, $X_{19}$ to $X_{23}$, $A_1$ and $A_2$ independently represent the same as in the formula (2); and $A_3$ represents a substituted or unsubstituted alkyl group including 1 to 20 carbon atoms, a substituted or unsubstituted cycloalkyl group including 3 to 18 ring carbon atoms, a substituted or unsubstituted alkoxy group including 1 to 20 carbon atoms, a substituted or unsubstituted cycloalkoxy group including 3 to 18 ring carbon atoms, a substituted or unsubstituted aryl group including 6 to 18 ring carbon atoms, a substituted or unsubstituted aryloxy group including 6 to 18 ring carbon atoms, a substituted or unsubstituted heteroaryl group including 5 to 18 ring atoms, a substituted or unsubstituted amino group, a substituted or unsubstituted silyl group, a fluoro group, or a cyano group.

6. The compound according to claim 2, which is a compound represented by the following formula (6):

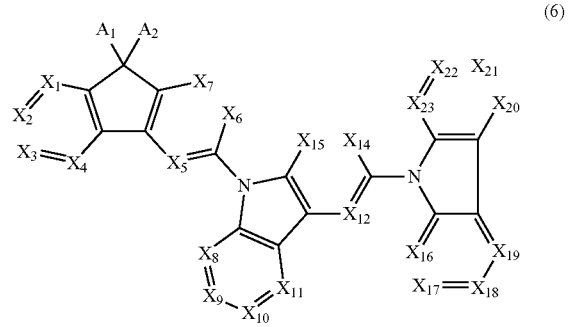

(6)

wherein $X_1$ to $X_{12}$, $X_{14}$ to $X_{23}$, $A_1$ and $A_2$ independently represent the same as in the formula (2).

7. The compound according to claim 1, wherein at least one of $X_1$ to $X_4$ and $X_7$ is N.

8. A material for an organic electroluminescence device comprising the compound according to claim 1.

9. An organic electroluminescence device comprising one or more organic thin film layers including an emitting layer between a cathode and an anode, wherein at least one layer of the organic thin film layers comprises the material for an organic electroluminescence device according to claim 8.

10. The organic electroluminescence device according to claim 9, wherein the organic emitting layer comprises the material for an organic electroluminescence device.

11. The organic electroluminescence device according to claim 9, wherein the organic emitting layer comprises a phosphorescent material, the phosphorescent material being an ortho-metalated complex of a metal atom selected from iridium (Ir), osmium (Os) and platinum (Pt).

12. The organic electroluminescence device according to claim 9, which comprises an electron-transporting region between the cathode and the emitting layer, the electron-transporting region comprising the material for an organic electroluminescence device.

13. The electroluminescence device according to claim 9, which comprises an electron-injecting layer between the organic emitting layer and the cathode, the electron-injecting layer comprising a nitrogen-containing ring derivative.

14. The compound according to claim 2, wherein at least one of $X_1$ to $X_4$ and $X_7$ is N.

15. The compound according to claim 4, wherein at least one of $X_1$ to $X_4$ and $X_7$ is N.

16. The compound according to claim 6, wherein at least one of $X_1$ to $X_4$ and $X_7$ is N.

\* \* \* \* \*

UNITED STATES PATENT AND TRADEMARK OFFICE
CERTIFICATE OF CORRECTION

PATENT NO. : 9,496,508 B2  
APPLICATION NO. : 14/363761  
DATED : November 15, 2016  
INVENTOR(S) : Takushi Shiomi, Ryohei Hashimoto and Hideaki Nagashima It is certified that error appears in the above-identified patent and that said Letters Patent is hereby corrected as shown below:

On the Title Page

Item (57), ABSTRACT, formula (1) should read:

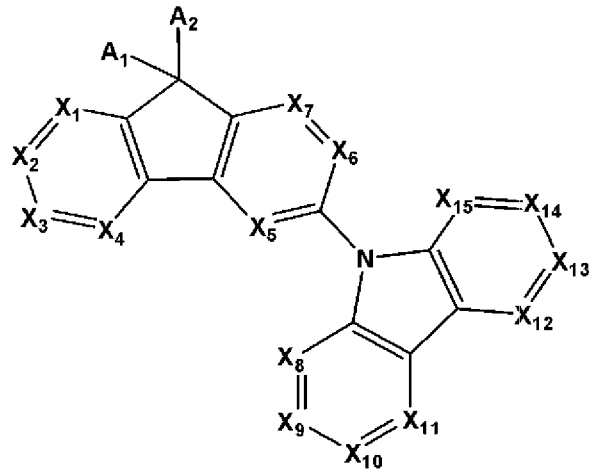

Signed and Sealed this  
Eighteenth Day of April, 2017

Michelle K. Lee  
*Director of the United States Patent and Trademark Office*

CERTIFICATE OF CORRECTION (continued)
U.S. Pat. No. 9,496,508 B2

In the Specification

Column 2, formula (1) should read:

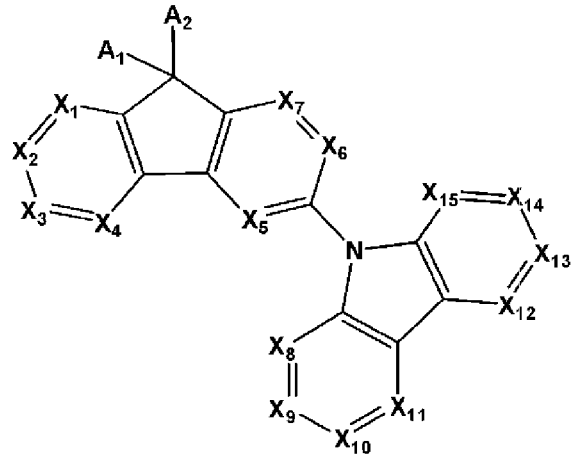

Column 3, formula (2) should read:

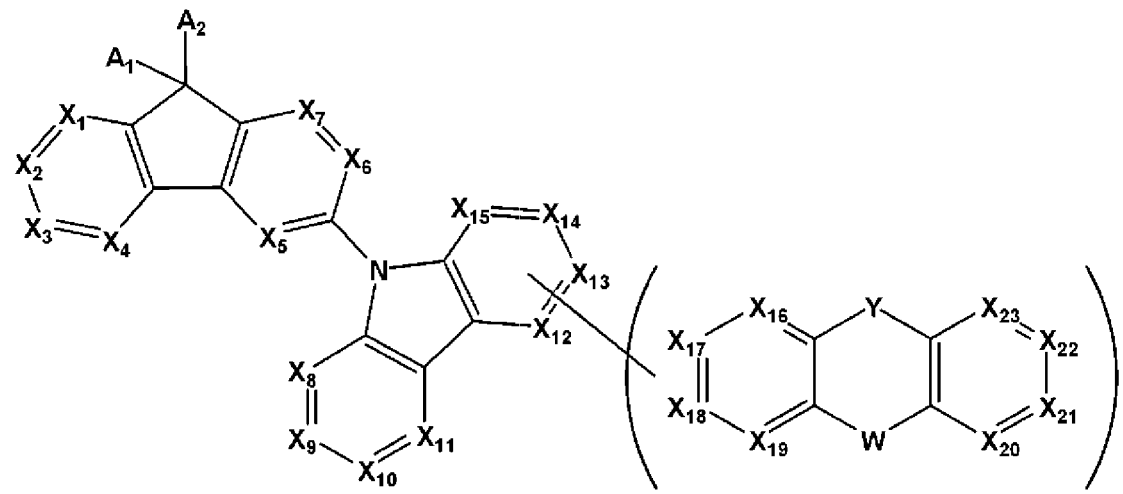

Column 5, formula (3) should read:

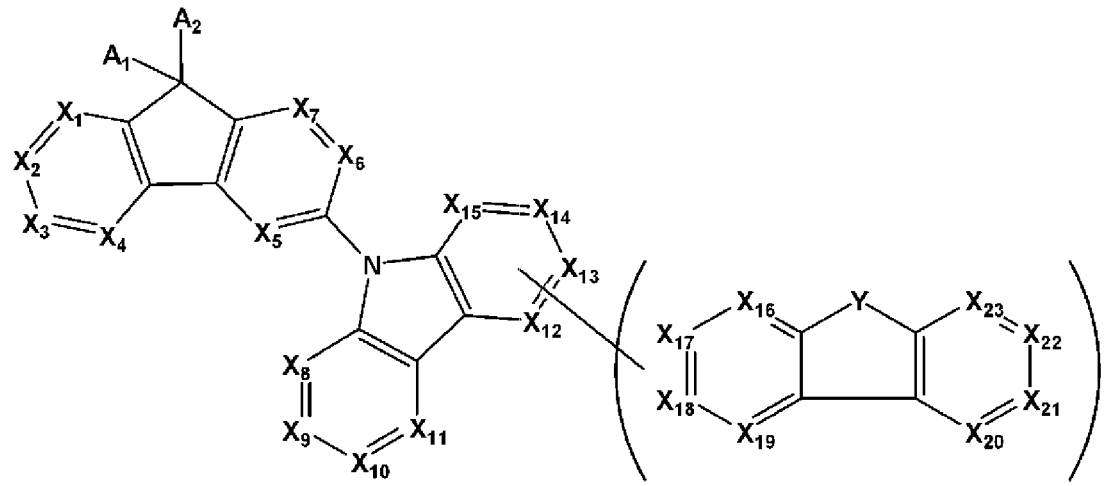

Column 5, formula (4) should read:
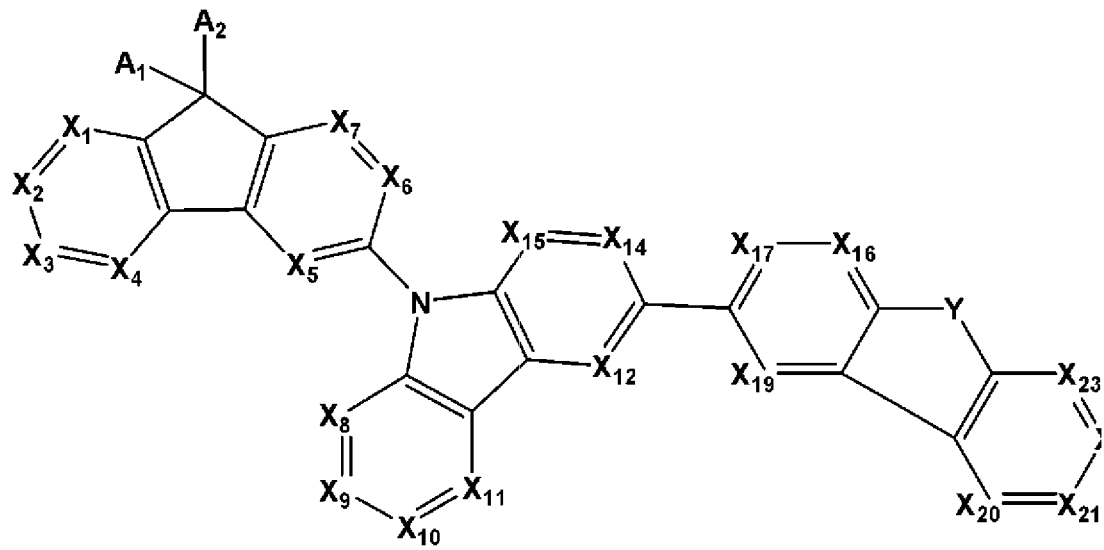
Column 5, formula (5) should read:
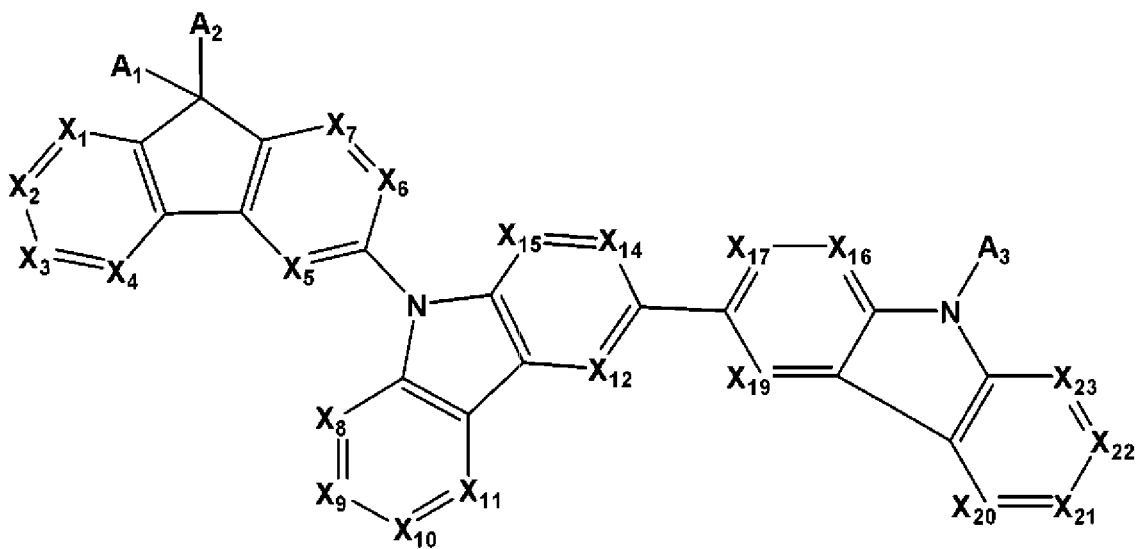

Column 6, formula (6) should read:
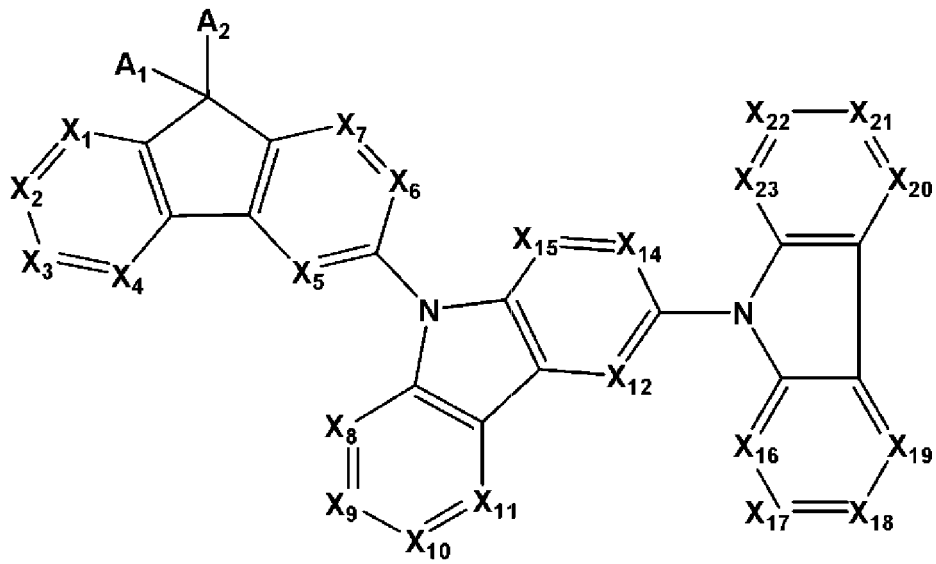
Column 7, formula (1) should read:
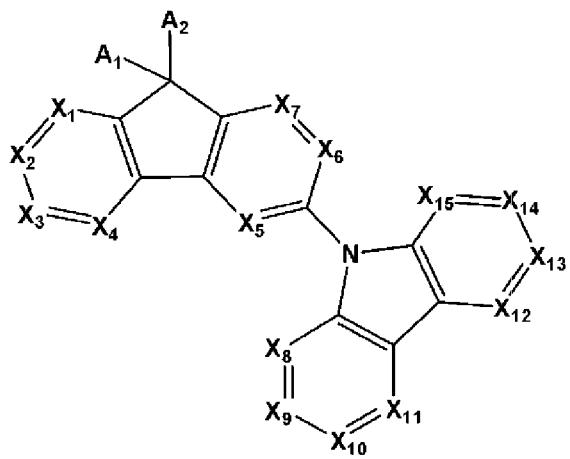
Column 8, formula (2) should read:
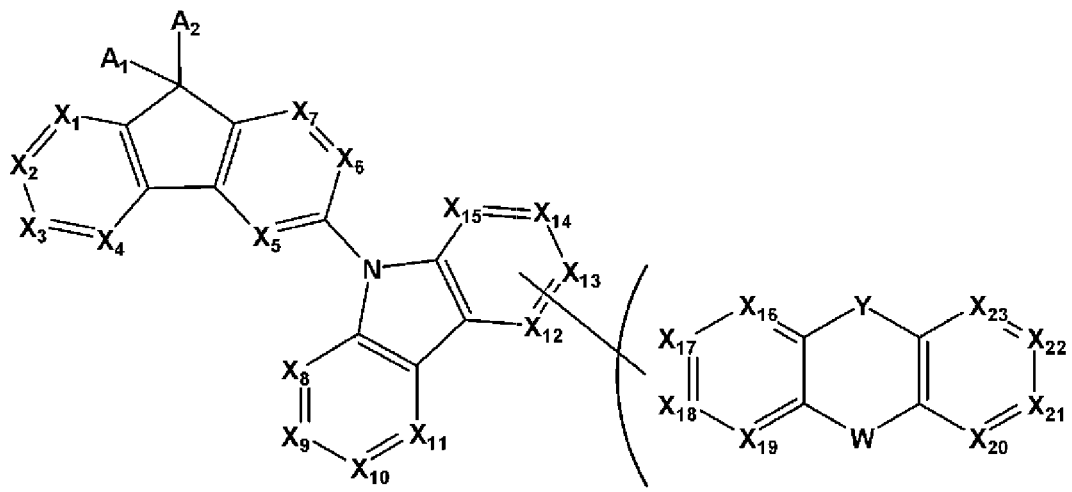

Column 10, formula (3) should read:
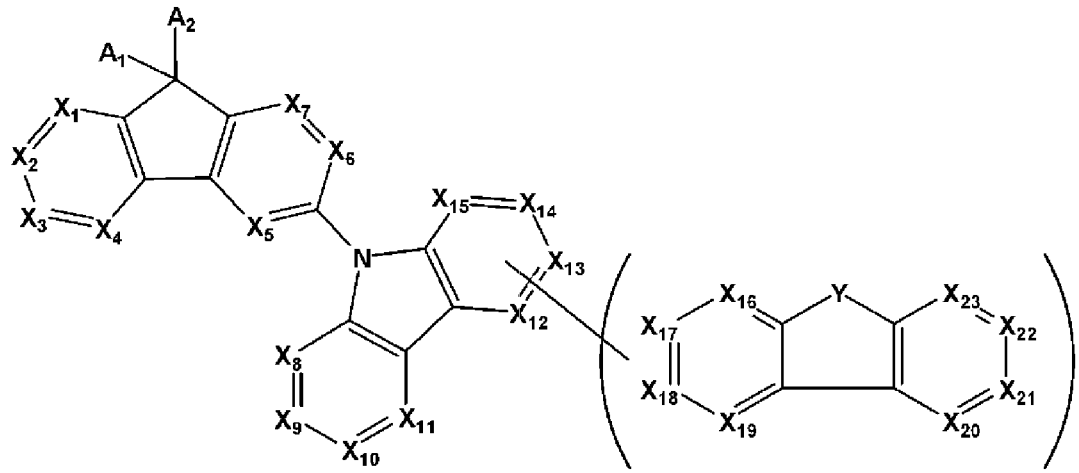
Column 10, formula (4) should read:
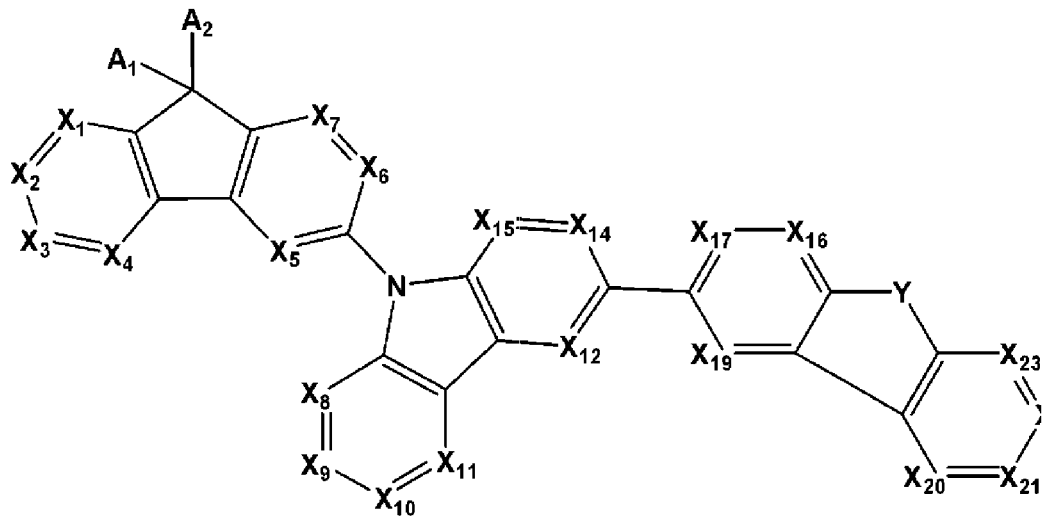
Column 10, formula (5) should read:
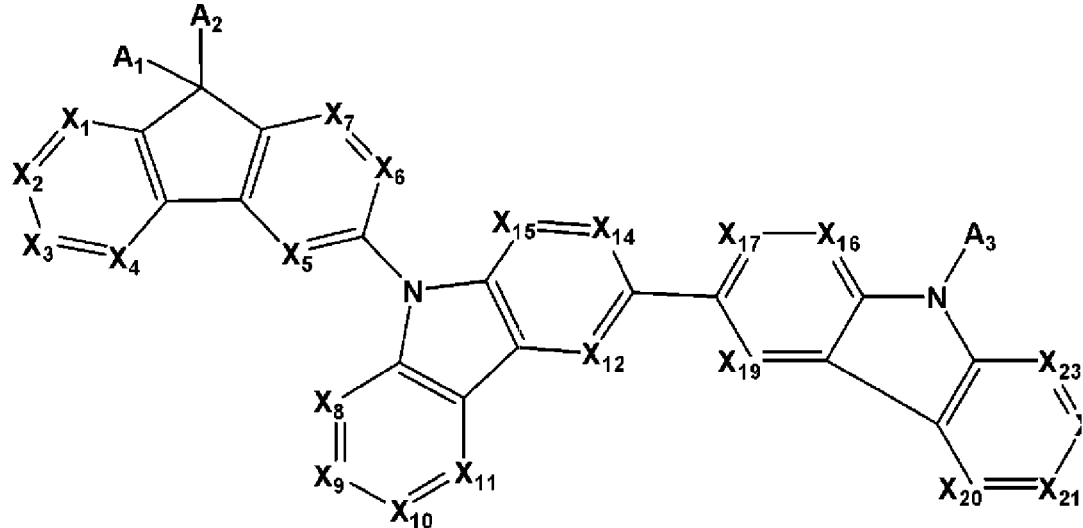

Column 11, at Lines 5-13, formula should read:
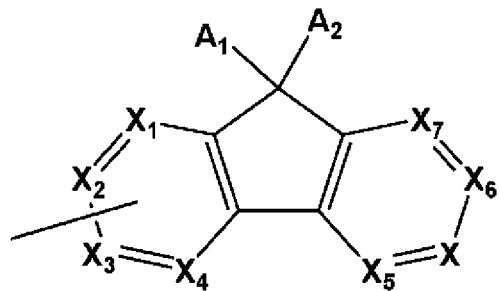
Column 11, formula (6) should read:
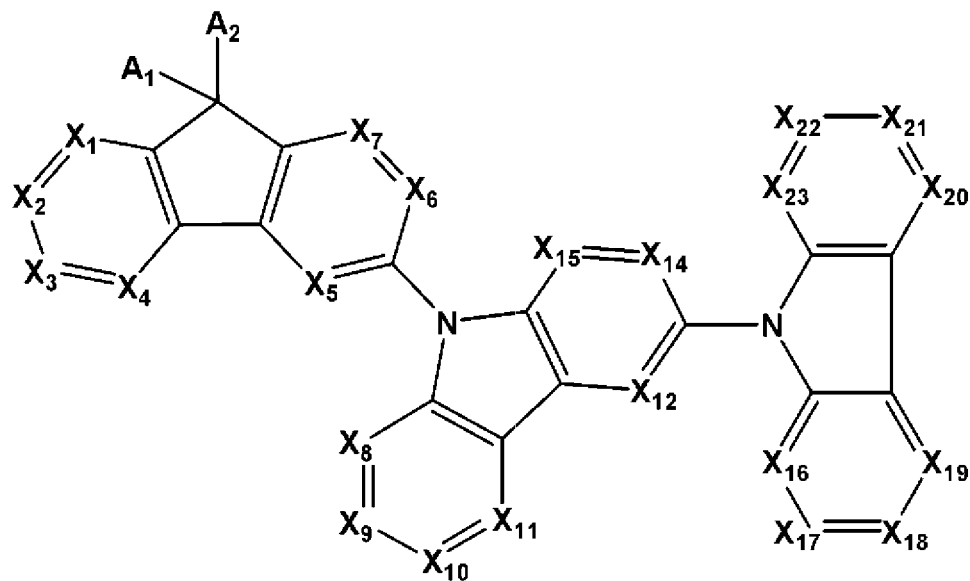
In the Claims
Column 51, formula (1) should read:
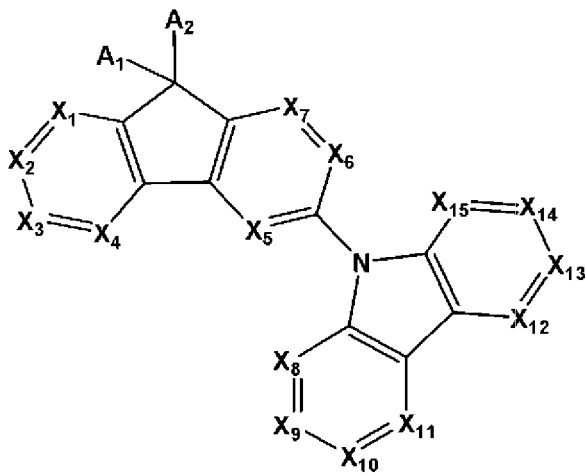

Column 52, formula (2) should read:
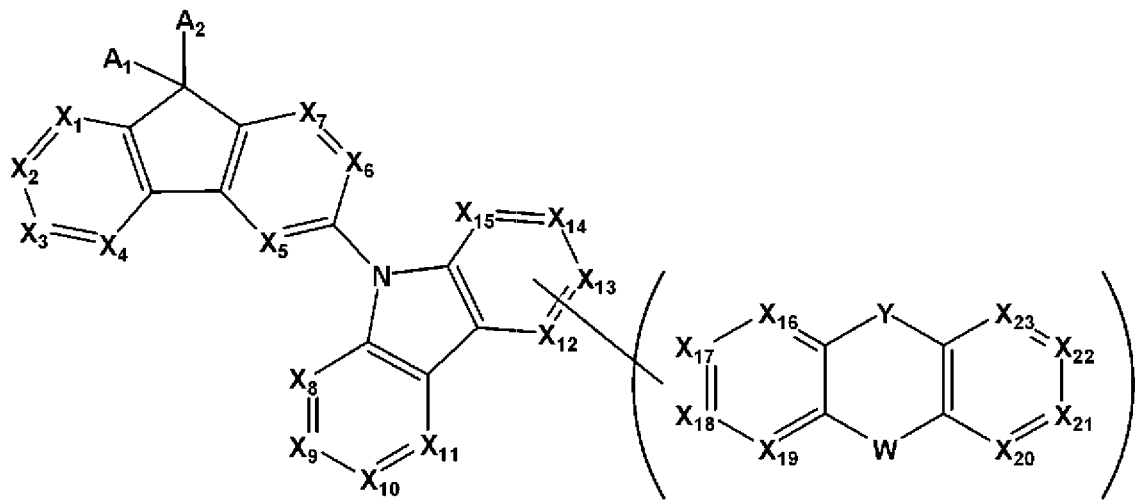
Column 53, formula (3) should read:
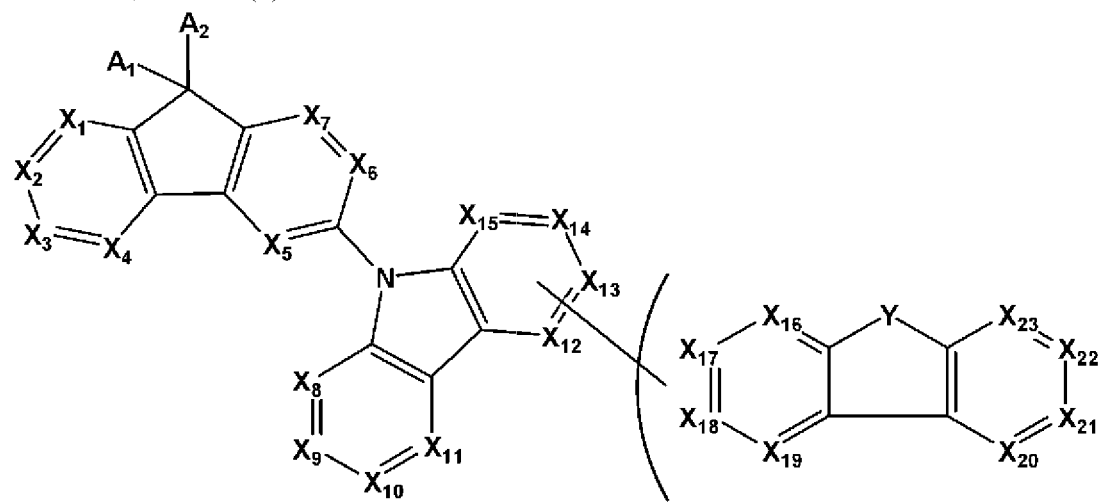
Column 54, formula (4) should read:
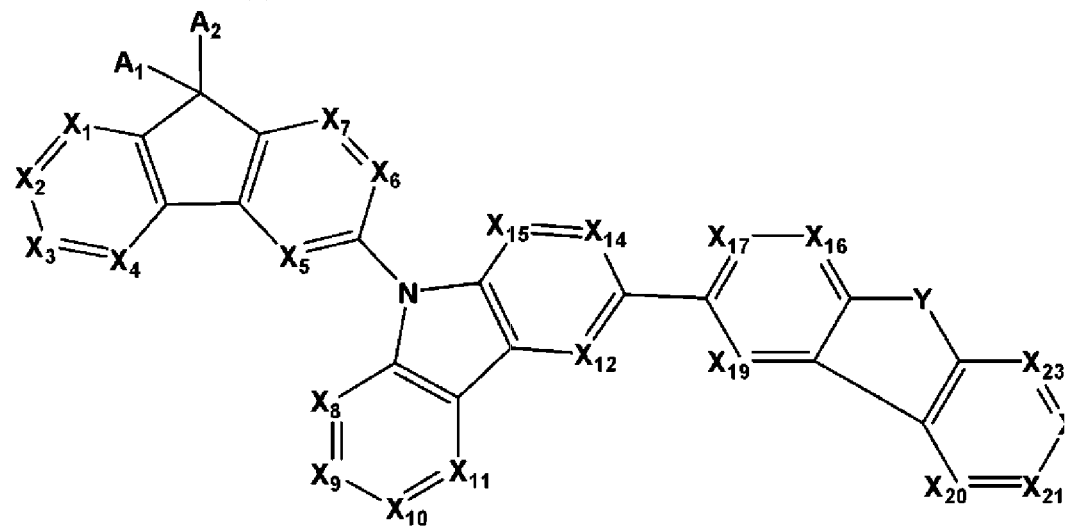

Column 54, formula (5) should read:
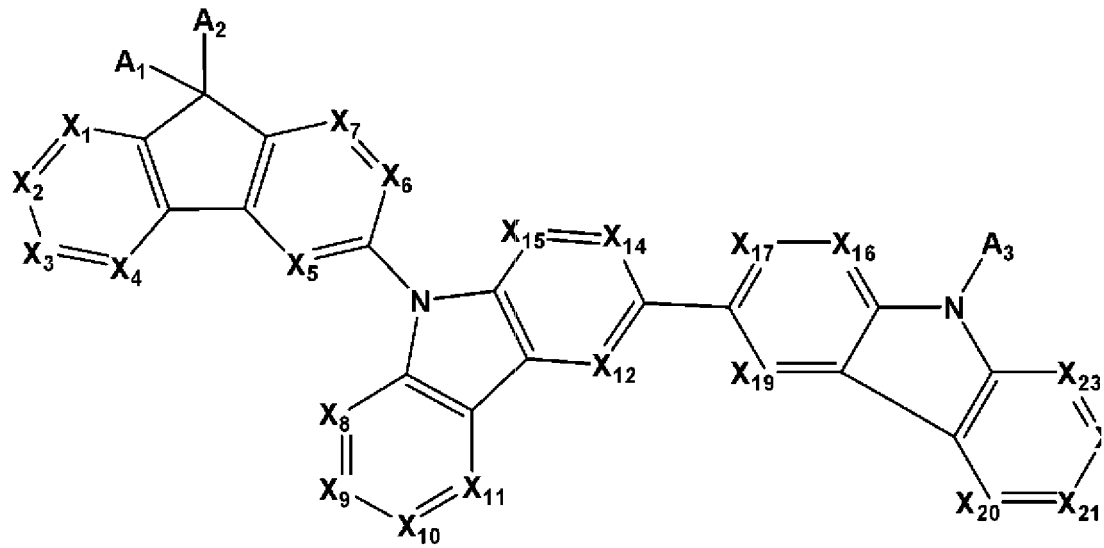
Column 54, formula (6) should read:
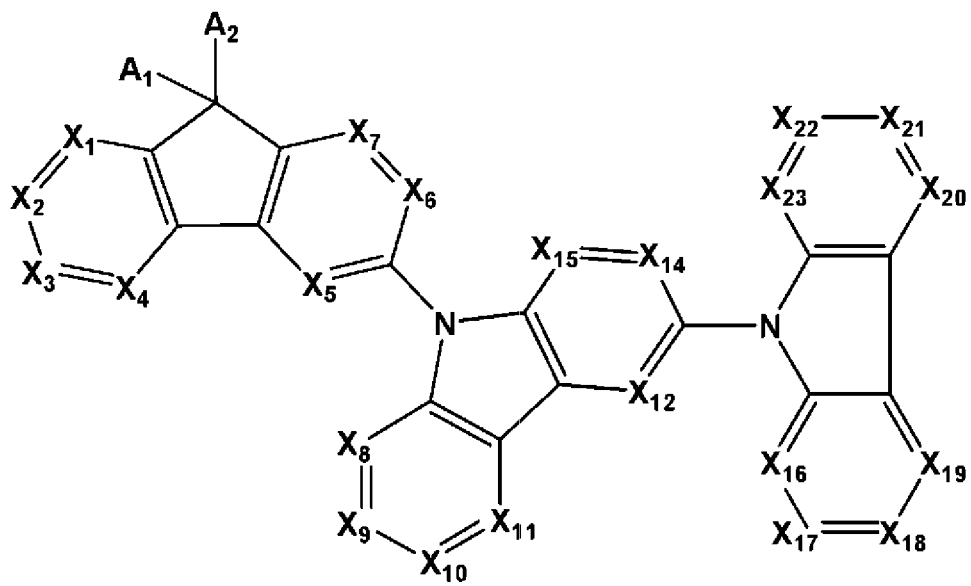
Column 54, Line 33, "$A_l$ and $A_2$" should read:
$A_1$ and $A_2$